(12) United States Patent
Grubbs et al.

(10) Patent No.: US 8,877,936 B2
(45) Date of Patent: Nov. 4, 2014

(54) RUTHENIUM OLEFIN METATHESIS CATALYSTS BEARING N-HETEROCYCLIC CARBENE LIGANDS WITH SUBSTITUTED BACKBONE

(75) Inventors: Robert H. Grubbs, South Pasadena, CA (US); Cheol Keun Chung, Westfield, NJ (US); Jean-Baptiste Bourg, Monrovia, CA (US); Kevin Kuhn, Annandale, VA (US)

(73) Assignee: California Institute of Technology, Pasadena, CA (US)

( * ) Notice: Subject to any disclaimer, the term of this patent is extended or adjusted under 35 U.S.C. 154(b) by 411 days.

(21) Appl. No.: 12/936,917

(22) PCT Filed: Apr. 9, 2009

(86) PCT No.: PCT/US2009/040109
§ 371 (c)(1),
(2), (4) Date: Feb. 7, 2011

(87) PCT Pub. No.: WO2009/126831
PCT Pub. Date: Oct. 15, 2009

(65) Prior Publication Data
US 2011/0124868 A1 May 26, 2011

Related U.S. Application Data

(60) Provisional application No. 61/118,171, filed on Nov. 26, 2008, provisional application No. 61/123,477, filed on Apr. 9, 2008.

(51) Int. Cl.
*C07F 15/00* (2006.01)
*C07D 233/06* (2006.01)
*C07C 6/04* (2006.01)
*C07C 67/475* (2006.01)
*C08G 61/08* (2006.01)
*C07C 67/333* (2006.01)

(52) U.S. Cl.
CPC .......... *C07D 233/06* (2013.01); *C07F 15/0046* (2013.01); *C07C 2101/10* (2013.01); *C07C 67/475* (2013.01); *C08G 61/08* (2013.01); *C07C 67/333* (2013.01)
USPC ............................ 548/103; 546/4; 548/354.1

(58) Field of Classification Search
CPC ........... C07F 15/0046; B01J 2231/543; C07D 233/06
USPC .................................. 546/4; 548/103, 354.1
See application file for complete search history.

(56) References Cited

U.S. PATENT DOCUMENTS

| | | |
|---|---|---|
| 6,610,626 B2 | 8/2003 | Grubbs et al. |
| 7,173,097 B2 | 2/2007 | Angeletakis |
| 2003/0144437 A1 | 7/2003 | Bell et al. |
| 2003/0236367 A1 | 12/2003 | Choi et al. |
| 2003/0236377 A1 | 12/2003 | Choi et al. |
| 2004/0167265 A1 | 8/2004 | Thompson et al. |
| 2007/0043188 A1 | 2/2007 | Schaubroeck et al. |
| 2007/0282148 A1* | 12/2007 | Berlin et al. ................... 585/645 |
| 2010/0145086 A1* | 6/2010 | Schrodi et al. ................. 554/124 |

FOREIGN PATENT DOCUMENTS

WO    WO 2008/046106 A2 *  4/2008  ............ C07C 67/347

OTHER PUBLICATIONS

International Search Report (ISR) and Written Opinion (WO) of the International Searching Authority, dated Jul. 6, 2009, in International Application No. PCT/US09/40109.
Office Action for Chinese Application No. 200980119030.1, dated Nov. 1, 2012.
Search Report for Chinese Application No. 200980119030.1, dated Nov. 1, 2012.
Hong et al., "Decomposition of Ruthenium Olefin Metathesis Catalysts", J. Am. Chem. Soc. 2007, vol. 129, pp. 7961-7968.
Hong et al., "Double C-H Activation of an N-Heterocyclic Carbene Ligand in a Ruthenium Olefin Metathesis Catalyst", Angew. Chem. Int. Ed. 2007, vol. 46, pp. 5148-5151.
Trnka et al., "Synthesis and Activity of Ruthenium Alkylidene Complexes Coordinated with Phosphine and N-Heterocyclic Carbene Ligands", J. Am. Chem. Soc. 2003, vol. 125, pp. 2546-2558.
Vehlow et al., "Deactivation of Ruthenium Olefin Metathesis Catalysts through Intramolecular Carbene-Arene Bond Formation", Angew. Chem. Ind. Ed. 2007, vol. 46, pp. 8082-8085.
Deshmukh et al., "Alkene metathesis: the search for better catalysts", Dalton Trans. 2007, pp. 2479-2491.
Stewart et al., "Increased Efficiency in Cross-Metathesis Reactions of Sterically Hindered Olefins", Org. Letters 2008, vol. 10, No. 3, pp. 441-444.
Stewart et al., "Highly Efficient Ruthenium Catalysts for the Formation of Tetrasubstituted Olefins via Ring-Closing Metathesis", Org. Letters 2007, vol. 9, No. 8, pp. 1589-1592.
Süβner et al., "π-Face donor properties of N-heterocyclic carbenes", Chem. Commun. 2005, pp. 5417-5419.
Hadei et al., "Electronic Nature of N-Heterocyclic Carbene Ligands: Effect on the Suzuki Reaction", Org. Letters 2005, vol. 7, No. 10, pp. 1991-1994.
Scholl et al., "Synthesis and Activity of a New Generation of Ruthenium-Based Olefin Metathesis Catalysts Coordinated with 1,3-Dimesityl-4,5-dihydroimidazol-2-ylidene Ligands", Org. Letters 1999, vol. 1, No. 6, pp. 953-956.
Schwab et al., "Synthesis and Applications of $RuCl_2(=CHR')(PR_3)_2$: The Influence of the Alkylidene Moiety on Metathesis Activity", J. Am. Chem. Soc. 1996, vol. 118, pp. 100-110.

(Continued)

*Primary Examiner* — Joseph Kosack

(57) ABSTRACT

This invention relates generally to olefin metathesis, more particularly, to tri- or tetra-substituted imidazolinium salts which are precursors to N-heterocyclic carbene (NHC) ligands with tri- or tetra-substituted imidazolinium rings, organometallic ruthenium complexes comprising gem di-substituted imidazolinium NHC ligands, organometallic ruthenium complexes comprising tri- or tetra-substituted imidazolinium NHC ligands, and to olefin metathesis methods using them. The catalysts and methods of the invention have utility in the fields of catalysis, organic synthesis, and industrial chemistry.

22 Claims, 15 Drawing Sheets

(56) References Cited

OTHER PUBLICATIONS

Schwab et al., "A Series of Well-Defined Metathesis Catalysts—Synthesis of [RuCl$_2$(=CHR')(PR$_3$)$_2$] and Its Reactions", Agnew. Chem. Int. Ed. Engl. 1995, vol. 34, No. 18, pp. 2039-2041.

Grubbs, "Handbook of Metathesis", Wiley-VCH, Weinheim, Germany, 2003, vol. 1, pp. v-xx.

Grubbs, "Handbook of Metathesis", Wiley-VCH, Weinheim, Germany, 2003, vol. 2, pp. v-xx.

Grubbs, "Handbook of Metathesis", Wiley-VCH, Weinheim, Germany, 2003, vol. 3, pp. v-xx.

Hoveyda et al., "The remarkable meta-catalysed olefin metathesis reaction", Nature, Nov. 8, 2007, vol. 450, pp. 243-251.

Schrodi et al., "Evolution and Applications of Second-Generation Ruthenium Olefin Metathesis Catalysts", Aldrichimica Acta 2007, vol. 40, No. 2, pp. 45-52.

Grubbs et al., "Olefin metathesis", Tetrahedron 2004, vol. 60, pp. 7117-7140.

Fürstner, "Olefin Metathesis and Beyond", Angew. Chem. Int. Ed. 2000, vol. 39, pp. 3012-3043.

Nicolaou et al., "Metathesis Reactions in Total Synthesis", Angew. Chem. Int. Ed. 2005, vol. 44, pp. 4490-4527.

Chung, Cheol K., and Robert H. Grubbs. "Olefin Metathesis Catalyst: Stabilization Effect of Backbone Substitutions of N-Heterocyclic Carbene." *Organic Letters* 10.13 (2008): 2693-2696.

Chung, Cheol K., and Robert H. Grubbs. "Supporting Information for Olefin Metathesis Catalyst: Stabilization Effect of Backbone Substitutions of N-Heterocyclic Carbene." S-1-S-27.

Kuhn, Kevin M., et al. "Effects of NHC-Backbone Substitution on Efficiency in Ruthenium-Based Olefin Metathesis." *Journal of the American Chemical Society* 131.14 (2009): 5313-5320.

* cited by examiner (1)

At 30 °C, $CD_2Cl_2$ (0.1 M)

At 60 °C, $C_6D_6$ (0.1 M)

(2)

At 30 °C, CD$_2$Cl$_2$ (0.1 M)

At 60 °C, C$_6$D$_6$ (0.1 M)

(3)

Eyring Plot

| (303 K) | H6 | H0 |
|---|---|---|
| $\Delta H^{\ddagger}$ (kcal/mol) | 11.9 (± 1.7) | 15.2 (± 0.8) |
| $\Delta S^{\ddagger}$ (e.u.) | −30 (± 6) | −19 (± 3) |
| $\Delta G^{\ddagger}$ (kcal/mol) | 21.0 (± 0.1) | 20.7 (± 0.01) |
| $k_{init}$ | $47 \times 10^{-4}$ | $67 \times 10^{-4}$ |

Minimum Overlap View of H6

Selected Bond Lengths [Å] and Angles [°] for H6

| | | | |
|---|---|---|---|
| Ru(1)-C(20) | 1.822(2) | C(20)-Ru(1)-C(1) | 98.53(8) |
| Ru(1)-C(1) | 1.959(2) | C(20)-Ru(1)-O(1) | 78.37(7) |
| Ru(1)-O(1) | 2.3068(14) | C(1)-Ru(1)-O(1) | 176.72(7) |
| Ru(1)-Cl(2) | 2.3354(5) | C(20)-Ru(1)-Cl(2) | 99.49(6) |
| Ru(1)-Cl(1) | 2.3549(5) | C(1)-Ru(1)-Cl(2) | 92.76(6) |
| | | O(1)-Ru(1)-Cl(2) | 88.85(4) |
| | | C(20)-Ru(1)-Cl(1) | 101.71(6) |
| | | C(1)-Ru(1)-Cl(1) | 90.98(6) |
| | | O(1)-Ru(1)-Cl(1) | 88.61(4) |
| | | Cl(2)-Ru(1)-Cl(1) | 157.668(19) |

RUTHENIUM OLEFIN METATHESIS CATALYSTS BEARING N-HETEROCYCLIC CARBENE LIGANDS WITH SUBSTITUTED BACKBONE

GOVERNMENT SUPPORT

This invention was supported by National Institutes of Health under Grant number GM031332. The U.S. government has certain rights in this invention.

CROSS REFERENCE TO RELATED APPLICATIONS

This application claims priority to PCT Application No. PCT/US09/40109, filed Apr. 9, 2009, which claims priority under 35 U.S.C. §119 to U.S. provisional application Ser. No. 61/118,171, filed Nov. 26, 2008; and U.S. provisional application Ser. No. 61/123,477, filed Apr. 9, 2008.

TECHNICAL FIELD

This invention relates generally to olefin metathesis, more particularly, to tri- or tetra-substituted imidazolinium salts which are precursors to N-heterocyclic carbene (NHC) ligands with tri- or tetra-substituted imidazolinium rings, organometallic ruthenium complexes comprising gem di-substituted imidazolinium NHC ligands, organometallic ruthenium complexes comprising tri- or tetra-substituted imidazolinium NHC ligands, and to olefin metathesis methods using them. The catalysts and methods of the invention have utility in the fields of catalysis, organic synthesis, and industrial chemistry.

BACKGROUND OF THE INVENTION

Olefin metathesis is an indispensable tool in making carbon-carbon bonds in modern organic synthesis. For recent reviews, see, e.g., (a) Grubbs, R. H. *Handbook of metathesis*; Wiley-VCH: Weinheim, Germany, 2003; (b) Hoveyda, A. H.; Zhugralin, A. R. *Nature* 2007, 450, 243-251; (c) Schrodi, Y.; Pederson, R. L. *Aidrichimica Acta* 2007, 40, 45-52; (d) Grubbs, R. H. *Tetrahedron* 2004, 60, 7117-7140; (e) Furstner, A. *Angew. Chem., Int. Ed.* 2000, 39, 3013-3043; (f) Nicolaou, K. C.; Bulger, P. G.; Sarlah, D. *Angew. Chem., Int. Ed.* 2005, 44, 4490-4527. Since the development of well-defined ruthenium-based metathesis catalysts, there has been significant effort directed towards improving the catalyst efficiency. Most notably, the substitution of a phosphine ligand of $RuCl_2(PCy_3)_2(=CHC_6H_5)$ for a bulky, electron-rich N-heterocyclic carbene (NHC) ligand led to metathesis catalysts with enhanced reactivity and stability. See, e.g., (a) Scholl, M.; Ding, S.; Lee, C. W.; Grubbs, R. H. *Org. Lett.* 1999, 1, 953-956; (b) Schwab, P.; Grubbs, R. H.; Ziller, J. W. *J. Am. Chem. Soc.* 1996, 118, 100-110; (c) Schwab, P.; France, M. B.; Ziller, J. W.; Grubbs, R. H. *Angew. Chem., Int. Ed.* 1995, 34, 2039-2041. the high reactivity of NHC complexes is often attributed to the superior electron donor ability of NHC ligands in comparison to the phosphine ligands. See, e.g., (a) Sussner, M. S.; Plenio, H. *Chem. Comm.* 2005, 5417-5419. (b) Hadei, N.; Kantchev, E. A. B.; O'Brien, C. J.; Organ, M. G. *Org. Lett.* 2005, 7, 1991-1994.)

In addition, the use of NHC ligand has allowed access to metathesis catalysts suitable for various applications through the modification of NHC ligand, such as water-soluble metathesis catalysts, solid-supported catalysts, and highly active catalysts suitable for hindered substrate. See, e.g., (a) Deshmukh, P. H.; Blechert, S. *Dalton Trans.* 2007, 2479-2491 and references therein; (b) Stewart, I. C.; Douglas, C. J.; Grubbs, R. H. *Org. Lett.* 2008, 10, 441-444; (c) Stewart, I. C.; Ung, T.; Pletnev, A. A.; Berlin, J. M.; Grubbs, R. H.; Schrodi, Y. *Org. Lett.* 2007, 9, 1589-1592.)

Although a variety of metathesis catalysts are available to address a range of problems in chemistry, it is still a challenge to obtain more robust catalysts that can be reliably applied in industrial processes. Ruthenium NHC complexes, albeit significantly more stable than the corresponding bisphosphine complexes, have limited lifetime. Recent catalyst stability studies suggested that C—H activation within the catalyst framework is responsible for the decomposition of the active ruthenium complexes. For instance, the X-ray structure of thermally degraded of ruthenium complexes bearing N-mesityl or N-phenyl-substituted NHC ligand revealed that the N-aryl substituents of NHC ligand have been altered by the metal center (Compounds C1-5 below). See, e.g., (a) Hong, S. H.; Wenzel, A. G.; Salguero, T. T.; Day, M. W.; Grubbs, R. H., *J. Am. Chem. Soc.* 2007, 129, 7961-7968. (b) Hong, S. H.; Chlenov, A.; Day, M. W.; Grubbs, R. H., *Angew. Chem., Int. Ed.* 2007, 46, 5148-5151. (c) Trnka, T. M.; Morgan, J. P.; Sanford, M. S.; Wilhelm, T. E.; Scholl, M.; Choi, T. L.; Ding, S.; Day, M. W.; Grubbs, R. H. *J. Am. Chem. Soc.* 2003, 125, 2546-2558. (d) Vehlow, K.; Gessler, S.; Blechert, S. *Angew. Chem., Int. Ed.* 2007, 46, 8082-8085.

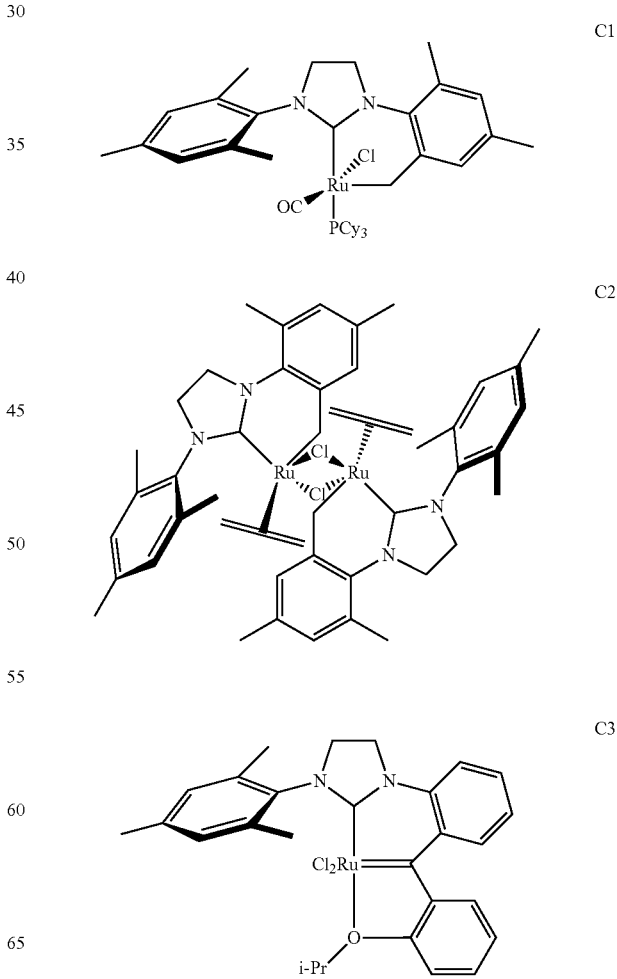

C4

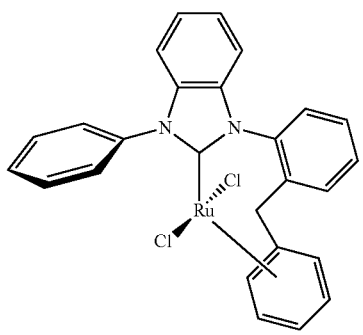

C5

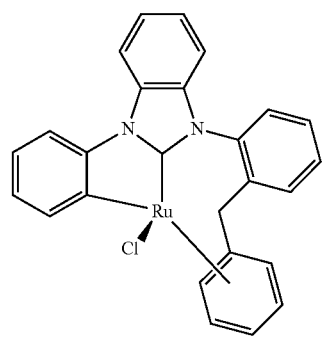

To resolve the above issue, this invention discloses further development of efficient and stable metathesis catalysts based on ruthenium NHC complexes.

SUMMARY OF THE INVENTION

The present invention relates to imidazolinium salt NHC ligand precursor of formula (I):

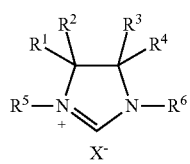

wherein:
a) $R^1$ and $R^4$ are methyl; and
$R^2$ and $R^3$ are independently selected from methyl, ethyl, or allyl, or $R^2$ and $R^3$ together with the carbons carrying them form a fused 6-, 7- or 8-membered carbocylic ring;
$R^5$ and $R^6$ are each independently a $C_1$-$C_{10}$ alkyl, cycloalkyl, a fused or bridged ring, aralkyl, or a group having the structure of formula (II);

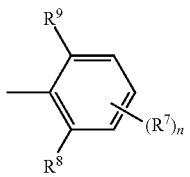

wherein,
n ranges from 1 to 3; with the proviso that only one of $R^5$ or $R^6$ may be a linear alkyl group having 3 or less carbons;
$R^7$ is independently selected from hydrogen, $C_1$-$C_{10}$ alkyl, $C_1$-$C_{10}$ alkoxy, aryl, aralkyl, and one or more functional groups;
$R^8$ and $R^9$ are independently selected from hydrogen, $C_1$-$C_{10}$ alkyl, fluoride or chloride; with the proviso that $R^8$ and $R^9$ are not $C_1$-$C_{10}$ alkyl at the same time; and,
wherein $R^2$ and/or $R^3$ may form a cyclic structure with one or both of $R^5$ and $R^6$, or through one or more links with at least one of $R^7$, $R^8$ and $R^9$; or,
b) $R^1$ is methyl;
$R^4$ is H;
$R^2$ and $R^3$ are independently selected from methyl, ethyl, allyl, or isopropyl, or $R^2$ and $R^3$ together with the carbons carrying them form a fused 6-, 7- or 8-membered carbocylic ring; with the proviso that $R^2$ and $R^3$ are not both isopropyl at the same time;
$R^5$ and $R^6$ are each independently a $C_1$-$C_{10}$ alkyl, cycloalkyl, a fused or bridged ring, aralkyl, or a group having the structure of formula (II);

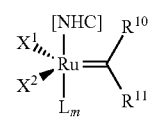

wherein,
n ranges from 1 to 3; with the proviso that only one of $R^5$ or $R^6$ may be a linear alkyl group having 3 or less carbons;
$R^7$ is independently selected from hydrogen, $C_1$-$C_{10}$ alkyl, $C_1$-$C_{10}$ alkoxy, aryl, aralkyl, and one or more functional groups;
$R^8$ and $R^9$ are independently selected from hydrogen, $C_1$-$C_{10}$ alkyl, fluoride or chloride; and,
wherein $R^2$ and/or $R^3$ may form a cyclic structure with one or both of $R^5$ and $R^6$, or through one or more links with at least one of $R^7$, $R^8$ and $R^9$; and,
$X^-$ is an anion for the imidazolinium salt.

The invention also relates to novel N-heterocyclic carbene (NHC) ruthenium olefin metathesis catalyst of formula (III):

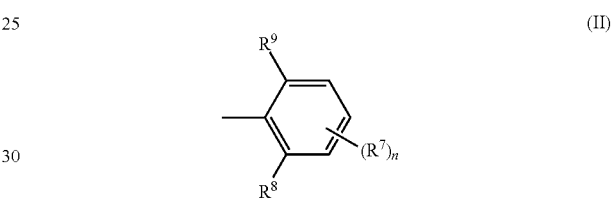

The catalysts of formula (III) contain the NHC ligand from the tri- or tetra-substituted imidizoladinium salt NHC ligand precursor described in formula (I) as well as the other ligands shown. The catalysts of formula (III) may also contain NHC ligands from gem di-substituted imidizoladinium salt NHC ligand precursors having the structure of formula (I) in which $R^1$ and $R^2$ are $C_1$-$C_{10}$ alkyl, or together form a cyclic structure, and $R^3$ and $R^4$ are hydrogen. In formula (III), $X^1$ and $X^2$ are independently anionic ligands; $R^{10}$ and $R^{11}$ are each independently hydrogen or a substituted or unsubstituted substituent selected from $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl; L is a neutral 2-electron donor ligand; and "m" is 1 or 2. $R^{10}$ and $R^{11}$ may optionally be linked together to form a cyclic structure via one of the substituents mentioned above. L may optionally be linked to $R^{11}$ to form a chelating carbene ligand.

Another embodiment of the invention relates to an olefin metathesis reaction which contacts an olefin with an N-heterocyclic carbene (NHC) ruthenium olefin metathesis catalyst of the invention under metathesis conditions. The catalysts of the invention may be used in, for example, ring-closing metathesis (RCM), cross metathesis (CM), ring-opening metathesis polymerization (ROMP), and acyclic diene metathesis polymerization (ADMET).

DETAILED DESCRIPTION OF THE INVENTION

1. Tri- and Tetra-Substituted Imidazolinium Salts

Figure 1:
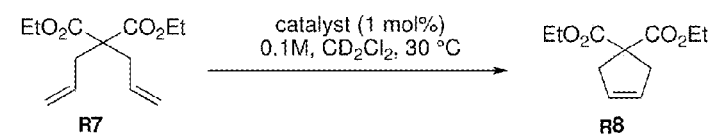
FIG. 1 depicts the standard activity tests of the Ruthenium catalysts in Ring Closing Metathesis (RCM) reactions to form a di-substituted olefin.
Figure 1:
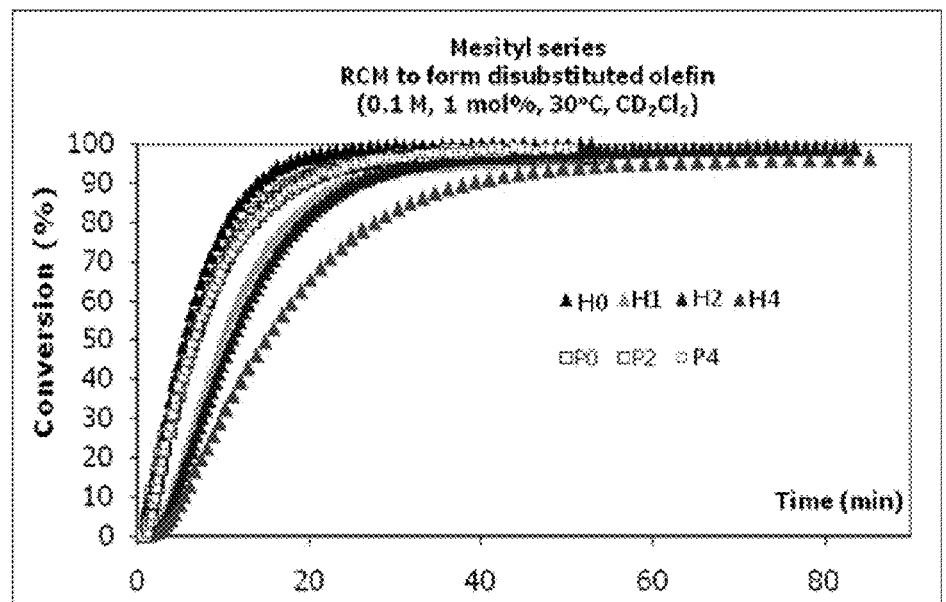

In the first embodiment, the invention relates to an imidazolinium salt NHC ligand precursor of formula (I):

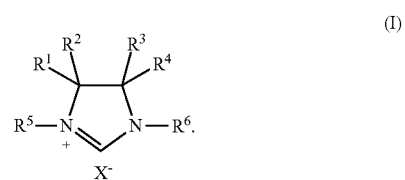

The imidazolinium salts of the invention may be tetra-substituted or tri-substituted on the backbone of the NHC ligand—the adjacent ring carbons of the imidazole ring. The substituents are defined by $R^1$, $R^2$, $R^3$ and $R^4$. As shown in the Scheme 1 below, restricting the N-aryl ring prevents the ruthenium complex comprising the NHC ligand from entering into the unwanted processes discussed above. The invention places bulky substituents, such as alkyl groups, on the backbone of the NHC ligands. In addition to the stabilization effect, the backbone substitution renders the NHCs more σ-donating than the non-substituted analogues, since it was conceivable that the direct backbone substitution would have greater influence on the donor ability of NHC than the substitution on the N-aryl groups.

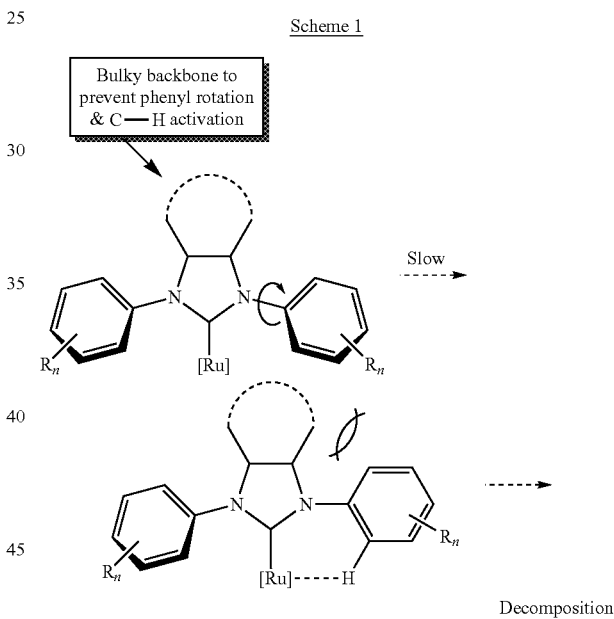

For tetra-substituted imidazolinium salts of the invention, $R^1$ and $R^4$ are methyl; $R^2$ and $R^3$ are independently selected from methyl, ethyl, or allyl, or $R^2$ and $R^3$ together with the carbons carrying them form a fused 6-, 7- or 8-membered carbocyclic ring; $R^5$ and $R^6$ are each independently a $C_1$-$C_{10}$ alkyl, cycloalkyl, a fused or bridged ring, aralkyl, or a group having the structure of formula (II):

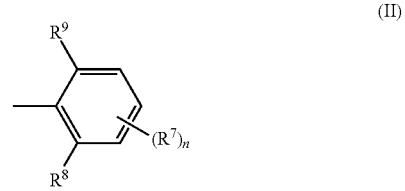

wherein n ranges from 1 to 3; with the proviso that only one of $R^5$ or $R^6$ may be a linear alkyl group having 3 or less carbons; $R^7$ is independently selected from hydrogen, $C_1$-$C_{10}$ alkyl, $C_1$-$C_{10}$ alkoxy, aryl, aralkyl, and one or more functional groups; $R^8$ and $R^9$ are independently selected from hydrogen, $C_1$-$C_{10}$ alkyl, fluoride or chloride: with the proviso that $R^8$ and $R^9$ are not $C_1$-$C_{10}$ alkyl at the same time; and wherein $R^2$ and/or $R^3$ may form a cyclic structure with one or both of $R^5$ and $R^6$, or through one or more links with at least one of $R^7$, $R^8$ and $R^9$; and $X^-$ is an anion for the imidazolinium salt.

For tri-substituted imidazolinium salts of the invention, $R^1$ is methyl; $R^4$ is H; $R^2$ and $R^3$ are independently selected from methyl, ethyl, allyl, or isopropyl, or $R^2$ and $R^3$ together with the carbons carrying them form a fused 6-, 7- or 8-membered carbocylic ring: with the proviso that $R^2$ and $R^3$ are not both isopropyl at the same time; $R^5$ and $R^6$ are each independently a $C_1$-$C_{10}$ alkyl, cycloalkyl, a fused or bridged ring, aralkyl, or a group having the structure of formula (II):

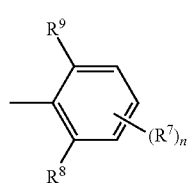

(II)

wherein n ranges from 1 to 3; with the proviso that only one of $R^5$ or $R^6$ may be a linear alkyl group having 3 or less carbons; $R^7$ is independently selected from hydrogen, $C_1$-$C_{10}$ alkyl, $C_1$-$C_{10}$ alkoxy, aryl, aralkyl, and one or more functional groups; $R^8$ and $R^9$ are independently selected from hydrogen, $C_1$-$C_{10}$ alkyl, fluoride or chloride; wherein $R^2$ and/or $R^3$ may form a cyclic structure with one or both of $R^5$ and $R^6$, or through one or more links with at least one of $R^7$, $R^8$ and $R^9$; and $X^-$ is an anion for the imidazolinium salt.

In preferred embodiments of these tri-substituted or tetra-substituted imidazolinium salts, $R^2$ and $R^3$ are methyl, or $R^2$ and $R^3$ together with the carbons carrying them form a fused 6-membered carbocylic ring; and $R^5$ and $R^6$ are independently selected from the group consisting of isopropyl, tert-butyl, neopentyl, phenyl, or a group having the structure of formula (II):

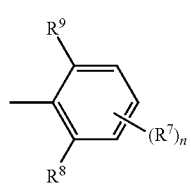

(II)

wherein n ranges from 1 to 3; $R^7$ is independently selected from hydrogen, $C_1$-$C_{10}$ alkyl, $C_1$-$C_{10}$ alkoxy, aryl, aralkyl, and one or more functional groups; and $R^8$ and $R^9$ are independently selected from hydrogen, $C_1$-$C_{10}$ alkyl, fluoride or chloride: with the proviso that $R^8$ and $R^9$ of the tetra-substituted imidazolinium salts are not $C_1$-$C_{10}$ alkyl at the same time. In even more preferred embodiments, $R^2$ and $R^3$ are methyl; $R^5$ and $R^6$ are independently selected from phenyl, mesityl, o-tolyl, m-tolyl, p-tolyl, o-difluorophenyl, o-dichlorophenyl or o-isopropylphenyl. For tetra-substituted imidazolinium salts, $X^-$ is preferably chloride, bromide, iodide, tetrafluoroborate ($BF_4$) or trifluoroacetate ($CF_3COO$); for tri-substituted imidazolinium salts $X^-$ is preferably chloride, tetrafluoroborate ($BF_4$) or trifluoroacetate ($CF_3COO$).

2. Preparation of Imidazolinium Salts

The tetra- or tri-substituted imidazolinium salts NHC ligand precursors of formulas (I) used to form the Ruthenium catalysts of the invention may be prepared from diamine derivatives bearing desired substituents and substitution pattern, as shown in the examples below. Typically, the diamine is dissolved in diethyl ether and treated with a solution of hydrogen chloride to precipitate the diamine hydrochloride salt. The diamine hydrochloride salt is reacted with large excess of triethyl orthoformate to give the desired imidazolinium chloride salts NHC ligand precursor of formula (I). Alternatively, the diamine compound can also form salt with trifluoroacetic acid or tetrafluoroboric acid, which is also reacted with large excess of triethyl orthoformate to give the desired imidazolidinium salts NHC ligand precursor of formula (I).

3. N-Heterocyclic Carbene (NHC) Ruthenium Catalysts of the Invention

The invention also relates to N-heterocyclic carbene (NHC) ruthenium olefin metathesis catalysts. Advantageously, the catalysts of the invention display greater efficiency/activity than current olefin metathesis catalysts for catalyzing ring-closing metathesis (RCM) reactions to form tetra-substituted cyclic olefins. The catalysts also perform the other known metathesis reactions in the family of metathesis reactions discussed above. The catalysts are also particularly useful in cross-metathesis to prepare tri-substituted olefins, and di-substituted olefins that are further substituted at the allylic carbon. The N-heterocyclic carbene (NHC) ruthenium olefin metathesis catalysts of the invention have the following general formula (III):

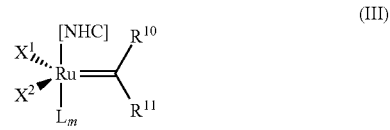

(III)

The NHC ligand in the ruthenium catalyst of formula (III) is derived from the imidazolinium salt NHC ligand precursor of formula (I) described above, with formula (IV):

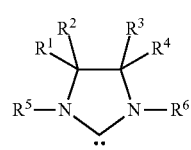

(IV)

For ruthenium catalyst derived from the tetra-substituted NHC ligand of the invention, $R^1$ and $R^4$ are methyl; $R^2$ and $R^3$ are independently selected from methyl, ethyl, or allyl, or $R^2$ and $R^3$ together with the carbons carrying them form a fused 6-, 7- or 8-membered carbocylic ring; $R^5$ and $R^6$ are each independently a $C_1$-$C_{10}$ alkyl, cycloalkyl, a fused or bridged ring, aralkyl, or a group having the structure of formula (II):

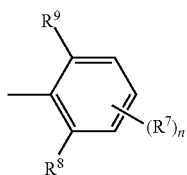

wherein n ranges from 1 to 3; with the proviso that only one of $R^5$ or $R^6$ may be a linear alkyl group having 3 or less carbons; $R^7$ is independently selected from hydrogen, $C_1$-$C_{10}$ alkyl, $C_1$-$C_{10}$ alkoxy, aryl, aralkyl, and one or more functional groups; $R^8$ and $R^9$ are independently selected from hydrogen, $C_1$-$C_{10}$ alkyl, fluoride or chloride: with the proviso that $R^8$ and $R^9$ are not $C_1$-$C_{10}$ alkyl at the same time; and wherein $R^2$ and/or $R^3$ may form a cyclic structure with one or both of $R^5$ and $R^6$, or through one or more links with at least one of $R^7$, $R^8$ and $R^9$.

For ruthenium catalyst derived from the tri-substituted NHC ligand of the invention, $R^1$ is methyl; $R^4$ is H; $R^2$ and $R^3$ are independently selected from methyl, ethyl, allyl, or isopropyl, or $R^2$ and $R^3$ together with the carbons carrying them form a fused 6-, 7- or 8-membered carbocylic ring: with the proviso that $R^2$ and $R^3$ are not both isopropyl at the same time; $R^5$ and $R^6$ are each independently a $C_1$-$C_{10}$ alkyl, cycloalkyl, a fused or bridged ring, aralkyl, or a group having the structure of formula (II):

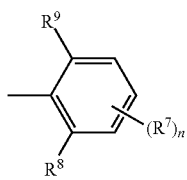

wherein n ranges from 1 to 3: with the proviso that only one of $R^5$ or $R^6$ may be a linear alkyl group having 3 or less carbons; $R^7$ is independently selected from hydrogen, $C_1$-$C_{10}$ alkyl, $C_1$-$C_{10}$ alkoxy, aryl, aralkyl, and one or more functional groups; $R^8$ and $R^9$ are independently selected from hydrogen, $C_1$-$C_{10}$ alkyl, fluoride or chloride. $R^2$ and/or $R^3$ may form a cyclic structure with one or both of $R^5$ and $R^6$, or through one or more links with at least one of $R^7$, $R^8$ and $R^9$.

In preferred embodiments of the ruthenium catalyst derived from the tri-substituted or tetra-substituted NHC ligand of the invention, $R^2$ and $R^3$ are methyl, or $R^2$ and $R^3$ together with the carbons carrying them form a fused 6-membered carbocylic ring; and $R^5$ and $R^6$ are independently selected from the group consisting of isopropyl, tertbutyl, neopentyl, phenyl, or a group having the structure of formula (II):

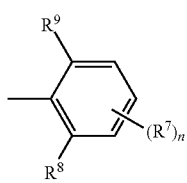

wherein n ranges from 1 to 3; $R^7$ is methyl, fluoride or chloride; and $R^8$ and $R^9$ are independently selected from hydrogen, $C_1$-$C_{10}$ alkyl, fluoride or chloride: with the proviso that $R^8$ and $R^9$ of the tetra-substituted imidazolinium salts are not $C_1$-$C_{10}$ alkyl at the same time. In even more preferred embodiments, $R^2$ and $R^3$ are methyl; and $R^5$ and $R^6$ are independently selected from phenyl, mesityl, o-tolyl, m-tolyl, p-tolyl, o-difluorophenyl, o-dichlorophenyl or o-isopropylphenyl.

One embodiment of the NHC ligand in the ruthenium catalyst of formula (III) of the invention includes the ruthenium catalyst derived from the gem di-substituted N-heterocyclic carbene (NHC) ligand of formula (IV):

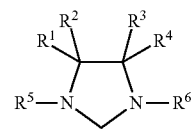

wherein $R^1$ and $R^2$ are $C_1$-$C_{10}$ alkyl, or together form a cyclic structure; $R^3$ and $R^4$ are H; $R^5$ and $R^6$ are each independently a $C_1$-$C_{10}$ alkyl, cycloalkyl, a fused or bridged ring, aralkyl, or a group having the structure of formula (II):

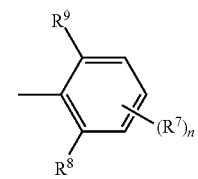

wherein, n ranges from 1 to 3: with the proviso that only one of $R^5$ or $R^6$ may be a linear alkyl group having 3 or less carbons; $R^7$ is independently selected from hydrogen, $C_1$-$C_{10}$ alkyl, $C_1$-$C_{10}$ alkoxy, aryl, aralkyl, and one or more functional groups; $R^8$ and $R^9$ are hydrogen, $C_1$-$C_{10}$ alkyl, fluoride or chloride. $R^1$ and/or $R^2$ may form a cyclic structure with one or both of $R^5$ and $R^6$, or through one or more links with at least one of $R^7$, $R^8$ and $R^9$.

In the catalysts of formula (III), $X^1$ and $X^2$ are independently anionic ligands. Preferably, $X^1$ and $X^2$ are halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, or $C_1$-$C_{20}$ alkylsulfinyl. Optionally, $X^1$ and $X^2$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, $X^1$ and $X^2$ are halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate. As discussed below, the other ligands in a catalyst of the invention, when substituted, may also contain such substituents. In even more preferred embodiments, $X^1$ and $X^2$ are each halide, $CF_3 CO_2$, $CH_3 CO_2$, $CFH_2 CO_2$, $(CH_3)_3 CO$, $(CF_3)_2 (CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride.

$R^{10}$ and $R^{11}$ are each independently hydrogen or a substituted or unsubstituted group selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ 20 alkylsulfonyl and $C_1$-$C_{20}$ alkylsulfinyl. Optionally, each of the $R^{10}$ or $R^{11}$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_{15}$ alkoxy, and phenyl. Moreover, $R^{10}$ and $R^{11}$, as well as any other of the catalyst ligands, may further include one or more functional groups as long as they do not defeat the activity of the catalyst. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. $R^{10}$ and $R^{11}$ may optionally be linked together to form a cyclic structure via one of the substituents mentioned above.

In preferred embodiments of these catalysts, the $R^{10}$ substituent is hydrogen, $C_1$-$C_5$ alkyl or aryl and the $R^{11}$ substituent is selected from the group consisting of $C_1$-$C_{20}$ alkyl, $C_2$-$C_{20}$ alkenyl, and aryl. In even more preferred embodiments, the $R^{11}$ substituent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments, $R^{11}$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^{11}$ substituent is phenyl or —CH=C($CH_3$)$_2$.

L may be any neutral 2-electron donor ligand known in the art. The variable "m" defines the number of neutral donor ligands, L. The variable "m" is 1 or 2 and preferably 1. When "m" is 1, L is any neutral 2-electron donor ligand. L may be linked to $R^{11}$ forming a chelating arbine ligand. When "m" is 2, L is a heteroarene ligand such as pyridine or substituted pyridine. See U.S. Pat. Nos. 6,759,537 and 6,818,586, herein incorporated by reference in their entirety; for examples of suitable heteroarene ligands. Preferably, the heteroarene ligand is pyridine or substituted pyridine.

In a preferred embodiment, L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L is a phosphine of the formula PR'R"R'", where R', R", and R'" are each independently aryl; $C_1$-$C_{10}$ alkyl (in particular, a primary or secondary alkyl); or $C_3$-$C_6$ cycloalkyl. In the most preferred embodiments, L is selected from the group consisting of P(cyclohexyl)$_3$, P(cyclopentyl)$_3$, P(isopropyl)$_3$, and P(phenyl)$_3$.

In a preferred embodiment, L may be linked to $R^{11}$ forming a chelating arbine ligand. The L portion of the chelating arbine ligand is still a 2-electron donor ligand when linked to $R^{11}$. L may or may not be linked to $R^{11}$ through a spacer moiety. U.S. Pat. No. 6,921,735 describes chelating arbine ligands and is incorporated herein by reference for examples of how the ligand and R substituent on the arbine can be linked through various spacer moieties. The spacer moiety may be substituted or unsubstituted.

Preferred catalysts of the invention where L and $R^{11}$ are linked include those represented by formula (V):

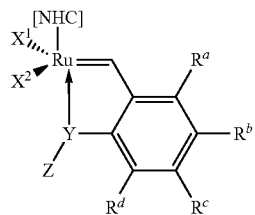

In formula (V), NHC is an N-heterocyclic carbene (NHC) ligand of formula (IV). Y is a heteroatom selected from oxygen, sulfur, nitrogen, or phosphorus. $X^1$ and $X^2$ are independently anionic ligands. Z is selected from hydrogen, alkyl, alkenyl, alkynyl, aryl, alkoxy, alkenyloxy, alkynyloxy, aryloxy, functionalized alkyl, or functionalized aryl, wherein the functional group(s) may independently be selected from alkoxy, aryloxy, halogen, carbonyl, carboxylic acid, ketone, aldehyde, nitrate, nitrile, nitro, cyano, isocyanate, hydroxyl, ester, ether, amine, imine, amide, sulfide, sulfonyl, sulfinyl, disulfide, sulfonate, carbamate, silane, siloxane, phosphine, phosphate, borate, or combinations thereof; each optionally substituted with an alkyl, halogen, alkoxy, aryl, aryloxy, or heteroaryl moiety. $R^a$, $R^b$, $R^c$, and $R^d$ are independently selected from hydrogen, halogen, alkyl, alkenyl, alkynyl, aryl, heteroaryl, alkoxy, alkenyloxy, alkynyloxy, aryloxy, functionalized alkyl, or functionalized aryl, wherein the functional group(s) may independently be selected from alkoxy, aryloxy, halogen, carbonyl, carboxylic acid, ketone, aldehyde, nitrate, nitrile, nitro, cyano, isocyanate, hydroxyl, ester, ether, amine, imine, amide, sulfide, sulfonyl, sulfinyl, disulfide, sulfonate, carbamate, silane, siloxane, phosphine, phosphate, borate, or combinations thereof; each optionally substituted with an alkyl, halogen, alkoxy, aryl, aryloxy, or heteroaryl moiety, wherein any two or more of $R^a$, $R^b$, $R^c$, and $R^d$ may be independently linked through hydrocarbon or functionalized hydrocarbon groups forming an aliphatic or aromatic ring.

Preferred catalysts of the invention where L and $R^{11}$ are linked may also include the following:

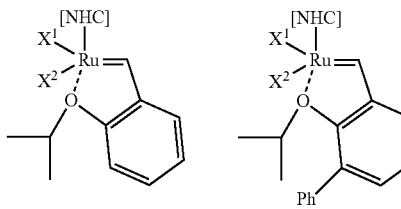

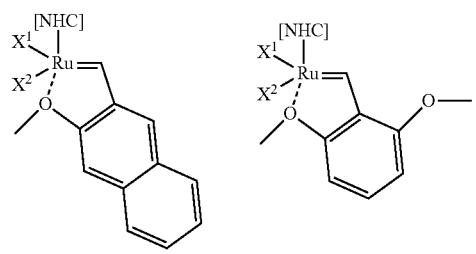

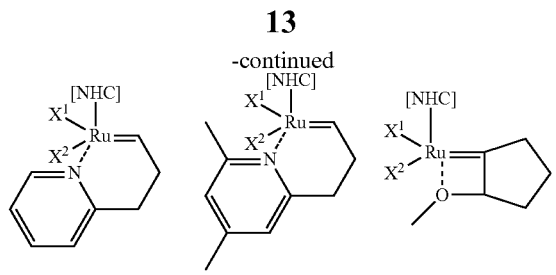

Examples of ruthenium complexes with chelating arbine ligands, ligands linking the L ligand and the R[11] substitutent, are also described in Kingsbury, J. S.; Harrity, J. P. A.; Bonitatebus, P. J., Jr.; Hoveyda, A. H. *J. Am. Chem. Soc.* 1999, 121, 791 and Garber, S. B.; Kingsbury, J. S.; Gray, B. L.; Hoveyda, A. H. *J. Am. Chem. Soc.* 2000, 122, 8168. Preferably, R[11] is linked to L via spacer group being 2-5 atoms in length between L and R[11], for example via an alkyl group, a cycloloalkyl group, or an aryl group. A preferred spacer group is a substituted or unsubstituted phenyl group.

4. Synthesis of Catalysts

The ruthenium catalysts of the invention may be prepared using methods known in the art. In general, the catalysts of the present invention are prepared via a ligand exchange reaction, for example, by substituting an NHC ligand for one of the neutral electron donor ligands in a first generation ruthenium carbene complexes (discussed above). For example, a Ruthenium Phosphine complex of the invention can be prepared by replacing a phosphine ligand in a complex of the general formula $(PCy_3)_2(X)_2Ru=CHC_6H_5$ with an NHC ligand described above. Example 2 illustrates preparation of ruthenium catalysts of the invention by this method. Ruthenium Ether complex of the invention can be prepared by replacing a phosphine ligand in a complex of the general formula $(PCy_3)(X)_2Ru=CH\text{-}o\text{-}iPrC_6H_5$ with an NHC ligand described above. Examples 3, 6 illustrate preparation of ruthenium catalysts of the invention by this method. As discussed in the Background of the Invention, these synthetic procedures are known in the art.

5. Metathesis Reactions

The ruthenium catalysts of the invention are particularly efficient olefin metathesis catalysts. Accordingly, one embodiment of the invention is an olefin metathesis reaction which contacts an olefin with an N-heterocyclic carbene (NHC) ruthenium olefin metathesis catalyst of the invention under metathesis conditions. The catalysts of the invention may be used in, for example, ring-closing metathesis (RCM), cross metathesis (CM), self metathesis (which is a type of cross metathesis), ring-opening metathesis polymerization (ROMP), and acyclic diene metathesis polymerization (ADMET).

The metathesis conditions for the catalysts of the invention are the same as those used in other olefin metathesis reactions and with other known olefin metathesis catalysts. Generally speaking, the olefin metathesis reactions are run at a temperature ranging from about 10° C. to about 70° C. and for a time period ranging from about 5 minutes to about 24 hours. The catalysts of the invention may be used in the same amounts as know for other olefin metathesis catalysts. Typically, about 1 to about 10 mol % of the catalyst is used and more often about 1 to 5 mol %.

The ruthenium catalysts of the invention are particularly useful in metathesis reactions for the production of tetra-substituted cyclic olefins. The catalysts of the invention have significantly increased efficiency/activity for the preparation of tetra-substituted cyclic olefins via olefin metathesis.

EXAMPLES

General Experimental Conditions for Examples 1-8

All reactions involving metal complexes were conducted in oven-dried glassware under a nitrogen atmosphere with anhydrous solvents, using standard Schlenk and glovebox techniques. Anhydrous solvents were obtained via elution through a solvent column drying system. (See Pangborn, A. B.; Giardello, M. A.; Grubbs, R. H.; Rosen, R. K.; Timmers, F. J. *Organometallics* 1996, 15, 1518-1520.) $RuCl_2(PCy_3)_2$ $(=CHC_6H_5)$ was obtained from Materia, Inc. Silica gel used for the purification of organometallic complexes was obtained from TSI Scientific, Cambridge, Mass. (60 Å, pH 6.5-7.0). NMR chemical shifts are reported in ppm downfield from $Me_4Si$, by using the residual solvent peak as internal standard for $^1H$ and $^{13}C$, and $H_3PO_4$ (δ 0.0) for $^{31}P$. Data for NMR spectra are reported as follows: chemical shift (δ ppm), multiplicity, coupling constant (Hz) and integration. IR spectra were recorded on a Perkin-Elmer Paragon 1000 Spectrophotometer. Gas chromatography data was obtained using an Agilent 6850 FID gas chromatograph equipped with a DB-Wax Polyethylene Glycol capillary column (J&W Scientific). X-ray crystallographic structures were obtained by the Beckman Institute X-ray Crystallography Laboratory of the California Institute of Technology. Unless otherwise stated, the screening of the catalysts, in ring-closing metathesis (RCM), cross metathesis (CM), and ring-opening metathesis polymerization reactions (ROMP), was conducted according to literature procedures. (see Ritter, T.; Hejl, A.; Wenzel, A. G.; Funk, T. W.; Grubbs, R. H. *Organometallics* 2006, 25, 5740-5745.) The initiation kinetics studies were conducted according to literature procedures. (see Sanford, M. S.; Love, J. A.; Grubbs, R. H. *J. Am. Chem. Soc.* 2001, 123, 6543-6554.)

Example 1

Preparation of NHC Ligand Precursors (S)

Procedure A:

A diethyl ether solution of the desired diamine was treated with a solution of hydrogen chloride (2 eq) to precipitate the diamine hydrochloride salt. The white solid was collected by filtration and washed with copious amount of diethyl ether. The solid was placed in a flask and triethyl orthoformate (large excess) was added. The resulting mixture was stirred at 130° C. for 5 to 10 min then cooled. After cooling to room temperature, the white solid was collected by filtration washing with large amount of diethyl ether and then with acetone to give the desired imidazolidinium chloride salt S.

Procedure B:

(See Jazzar, R.; Bourg, J.-B.; Dewhurst, R. D.; Donnadieu, B.; Bertrand, G. J. Org. Chem. 2007, 72, 3492-3499) To a THF solution (40 mL) of the corresponding formamidine, (1 eq) at −78° C. was added a solution of n-BuLi in hexanes (1 eq). The mixture was stirred for 30 minutes, then was allowed to warm to r.t. and stirred for a further 12 hours. The mixture was again cooled to −78° C., and 3-bromopropene (1 eq) or 3-bromo-2-methylpropene (1 eq) was slowly added. The mixture was stirred for 30 minutes at −78° C. then heated at 50° C. for 12 hours. Removal of the volatiles under vacuum and extraction with hexanes afforded the corresponding alkylated derivative.

An oven dried, argon flushed, sealable Schlenk tube with a Teflon stopcock was loaded with the alkylated derivative (1 eq), toluene and was cooled to 0° C., at which point was added a solution of HCl in Et$_2$O (2.0 M, 1 eq). Precipitation of a white powder was immediately observed. After 15 minutes at 0° C. the mixture was left to warm to r.t. and stirred for an additional 15 minutes. The mixture was heated at 110° C. for 24 hours, after which time the volatiles were removed under vacuum and the resulting salt washed with toluene and ether to afford the desired imidazolinium salts.

Example 1a 1,3-Dimesityl-4-Methyl-imidazolinium chloride (S1

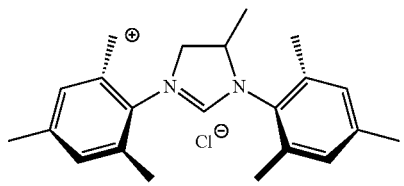

S1

Prepared according to procedure B. $^1$H NMR (500 MHz, CDCl$_3$): δ 9.70 (s, 1H), 6.88 (m, 4H), 5.02 (m, 1H), 4.75 (pseudo-t, J=11.5 Hz, 1H), 3.85 (dd, J=8.5 Hz, J=12.0 Hz, 1H), 2.40-2.10 (m, 18H), 1.50 (d, J=6.5 Hz, 3H). $^{13}$C NMR (75 MHz, CDCl$_3$): δ 159.8, 140.4, 140.2, 135.8, 135.3, 135.1, 134.8, 130.4, 130.3, 130.2, 130.1, 130.0 (br s), 128.8, 60.5, 58.3, 21.1, 21.0, 19.0, 18.8, 18.5, 18.0 (br s). HRMS Calc'd for C$_{22}$H$_{29}$N$_2$: 321.2331. Meas: 321.2321.

Example 1b 1,3-dimesityl-4,4-Dimethyl-imidazolinium chloride (S2

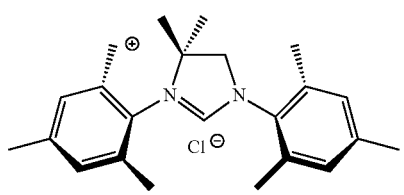

S2

Compound S2 is described in the literature. (See Jazzar, R.; Bourg, J.-B.; Dewhurst, R. D.; Donnadieu, B.; Bertrand, G. J. Org. Chem. 2007, 72, 3492-3499)

Example 1c (Cis-4,5)-1,3-dimesityl-4,5-Dimethyl-imidazolinium chloride (S3)

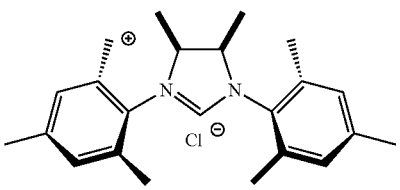

S3

Prepared according to procedure A. $^1$H NMR (300 MHz, CDCl$_3$): δ 9.77 (s, 1H), 6.98 (s, 2H), 6.96 (s, 2H), 5.13 (m, 2H), 2.43 (s, 12H), 2.39 (s, 12H), 2.29 (s, 6H), 1.33 (d, J=6.0 Hz, 6H). $^{13}$C NMR (75 MHz, CDCl$_3$): δ 159.0, 140.3, 135.8, 135.4, 130.4, 130.3, 129.0, 62.4, 21.1, 19.1, 18.7, 12.4. HRMS Calc'd for C$_{23}$H$_{31}$N$_2$: 335.2487. Meas: 335.2495.

Example 1d 1,3-dimesityl-4,4,5-trimethyl-imidazolinium tetrafluoroborate (S4)

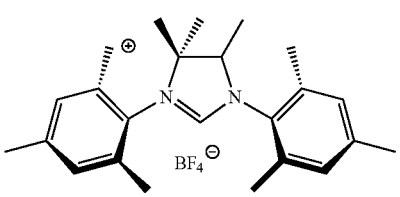

S4

A mixture of diamine (1.62 g, 4.78 mmol), ammonium tetrafluoroborate (0.75 g, 7.17 mmol), and triethyl orthoformate (12 ml) was stirred at 120° C. for 10 min and cooled to room temperature. The precipitation was collected by filtration, and the solid was redissolved in CH$_2$Cl$_2$. After the insoluble material was filtered off, the filtrate was evaporated under vacuum, and the residue was recrystallized in ethyl acetate to give S4 as a white solid (543 mg, 1.24 mmol, Y=26%). $^1$H NMR (300 MHz, DMSO-d6): δ 9.00 (s, 1H), 7.13 (s, 2H), 7.11 (s, 2H), 4.71 (q, J=6.9 Hz, 1H), 2.34-2.29 (m, 18H), 1.52 (s, 3H), 1.36 (s, 3H), 1.19 (d, J=6.9 Hz, 3H). $^{13}$C NMR (75 MHz, DMSO-d6): δ 159.0, 139.7, 137.5, 136.9, 136.0, 135.8, 130.2, 130.1, 129.8, 129.2, 128.3, 73.5, 67.7, 26.3, 20.5, 20.5, 19.3, 19.1, 18.2, 17.9, 11.9. $^{19}$F NMR (282 MHz, DMSO-d6): δ −148.7. HRMS Calc'd for $C_{24}H_{33}N_2$: 349.2644. Meas: 349.2648.

Example 1e 1,3-bis(2,6-difluorophenyl)-4,4,5,5-tetramethyl-imidazolin-2-ium chloride (S5)

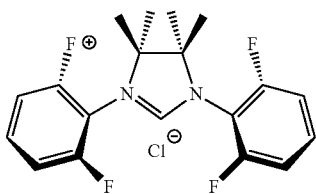

S5

A mixture of diamine (370 mg, 0.895 mmol) and triethyl orthoformate (3 ml) was heated at 130° C. for 1.5 hr, then cooled to room temperature. White solid which was formed on adding diethyl ether, was collected by filtration (80 mg, 0.207 mmol, Y=23%). $^1$H NMR (300 MHz, DMSO-d6): δ 9.56 (s, 1H), 7.81-7.74 (m, 2H), 7.54-7.49 (m, 4H), 1.44 (s, 12H). $^{19}$F NMR (282 MHz, DMSO-d6): δ −117.3. HRMS Calc'd for $C_{19}H_{19}F_4N_2^+$: 351.1484. Meas: 351.1472.

Example 1f 1,3-diphenyl-4,4,5,5-tetramethyl-imidazol-2-ium chloride (S6)

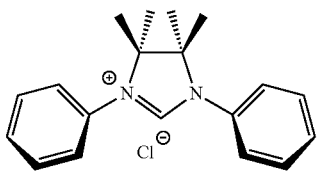

S6

A mixture of 2,3-butandione (5.00 g, 58.0 mmol), aniline (10.80 g, 116 mmol), and ethanol (ca. 5 ml) was stirred at room temperature for 1 day. The yellow crystalline solid was collected by filtration and rinsed with a small amount of ethanol to yield 10.41 g (44.1 mmol, Y=76%) of the desired diimine. A solution of the diimine (3.14 g, 13.29 mmol) in dry benzene was placed in a flask equipped with a reflux condenser, and added a solution of methylmagnesium chloride in tetrahydrofuran (3.0 M, 17.7 ml, 53.2 mmol). The resulting solution was stirred at refluxing temperature for overnight. After cooled to room temperature, the reaction mixture was slowly added saturated aqueous solution of ammonium chloride. The organic layer was separated and the aqueous layer was extracted with ethyl acetate three times. The combined organic layer was washed with brine, dried over magnesium sulfate, and purified by flash chromatography on silica (eluent: hexanes/ethyl acetate=30/1) to yield the desired diamine as a yellow oil (1.32 g, 4.90 mmol, Y=37%). The diamine was dissolved in diethyl ether (10 ml) and treated with a solution of hydrogen chloride (4 M in dioxane) to precipitate the diamine hydrochloride salt. The solid collected by filtration was added triethyl orthoformate (1.5 ml) and stirred at 120° C. for 17 hours. After cooled to room temperature, the tan colored solid was collected by filtration and washed with diethyl ether and acetone to give the desired imidazolidinium chloride salt S6 as a white powder (1.12 g, 3.56 mmol, Y=73%). $^1$H NMR (300 MHz, CD$_2$Cl$_2$): δ 9.37 (s, 1H), 7.69-7.66 (m, 4H), 7.54-7.52 (m, 6H), 1.46 (s, 12H). $^{13}$C NMR (75 MHz, CD$_2$Cl$_2$): δ 156.8, 133.3, 130.4, 130.0, 128.6, 74.0, 21.5. HRMS Calc'd for $C_{19}H_{23}N_2$: 279.1861. Meas: 279.1852.

Example 1g 1,3-di-o-tolyl-phenyl-4,4,5,5-tetramethyl-imidazol-2-ium chloride (S7)

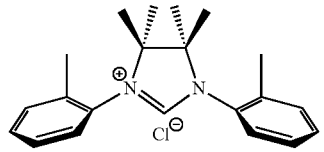

S7

A mixture of 2,3-butandione (2.00 g, 23.23 mmol), o-tuluidine (5.00 g, 46.66 mmol), and ethanol (ca. 2 ml) was stirred at room temperature for 1 day. The yellow crystalline solid was collected by filtration and rinsed with a small amount of ethanol to yield 3.42 g (12.97 mmol, Y=56%) of the desired diimine. A solution of the diimine (3.00 g, 11.35 mmol) in dry benzene was placed in a flask equipped with a reflux condenser, and added a solution of methylmagnesium chloride in tetrahydrofuran (3.0 M, 11.3 ml, 45.4 mmol). The resulting solution was stirred at refluxing temperature for overnight. After cooled to room temperature, the reaction mixture was slowly added saturated aqueous solution of ammonium chloride. The organic layer was separated and the aqueous layer was extracted with ethyl acetate three times. The combined organic layer was washed with brine, dried over magnesium sulfate, and purified by flash chromatography on silica (eluent: hexanes/ethyl acetate=30/1) to yield the desired diamine as a yellow oil (2.25 g, 7.60 mmol, Y=67%). The diamine was dissolved in diethyl ether (10 ml) and treated with a solution of hydrogen chloride (4 M in dioxane) to precipitate the diamine hydrochloride salt. The solid was collected by filtration and rinsed with ample amount of diethyl ether then with acetone to give the desired amine salt as a white powder (2.19 g, 5.93 mmol, Y=78%). A mixture of the diamine salt (330 mg, 0.89 mmol) and triethyl orthoformate (1.5 ml) was placed in a vial and stirred at 120° C. for 18 hours. After cooled to room temperature, the tan colored solid was collected by filtration and washed with diethyl ether. (S7, 64 mg, 0.187 mmol, Y=21%). $^1$H NMR (300 MHz, CDCl$_3$): δ 9.38 (br s, 1H), 7.58 (deformed d, 2H), 7.40-7.30 (m, 6H), 2.47 (s, 6H), 1.50 (s, 12H). $^{13}$C NMR (75 MHz, CDCl$_3$): δ

157.9, 136.3, 131.8, 131.3, 130.4, 130.4, 127.2, 74.0, 21.6, 18.8. HRMS Calc'd for $C_{21}H_{27}N_2$: 307.2174. Meas: 307.2162.

Example 1h

1-Mesityl-4,4-dimethyl-3-phenyl-4,5-dihydro-1H-imidazol-2-ium chloride (S8)

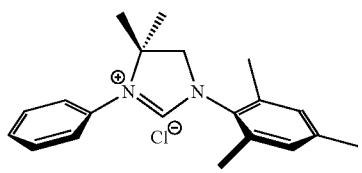

S8

2-bromo-2-methylpropanoyl bromide (4.50 g, 19.57 mmol) was added to a mixture of 2,4,6-trimethylaniline (2.41 g, 17.78 mmol), triethylamine (3.60 g, 35.56 mmol), and $CH_2Cl_2$ (20 ml) at 0° C. under Ar atmosphere. The cooling bath was removed after the addition was completed, and the reaction mixture was stirred at room temperature for 1.5 hour, after which time the mixture was diluted with $CH_2Cl_2$ (20 ml) and added aqueous solution of $NH_4Cl$. After the aqueous phase was separated, the organic layer was washed with brine and dried over anhydrous $MgSO_4$. Filtration and concentration of the filtrate gave 2-bromo-N-mesityl-2-methylpropanamide as a pale yellow solid (5.05 g, 17.78 mmol, 100%). A solution of this amide (284 mg, 1.00 mmol) in dry THF (5 ml) was added to a mixture of sodium hydride (60% in mineral oil, 80 mg, 2.00 mmol), aniline (112 mg, 1.20 mmol) and THF (5 ml), and the resulting mixture was stirred for overnight at room temperature. The mixture was then added an aqueous solution of $NH_4Cl$ (15 ml), extracted with ethyl acetate (20 ml×2), and the combined organic layer was washed with brine then dried over anhydrous $Na_2SO_4$. After filtration, the filtrate was concentrated under vacuum, and the residue was purified by column chromatography on silica (eluent: Hexane/Ethyl acetate=5/1~4/1) to give the amide as a white solid (255 mg, 0.86 mmol, Y=86%). $^1$H NMR (300 MHz, $CDCl_3$): δ 8.35 (s, 1H), 7.25-7.17 (m, 2H), 6.84-6.71 (m, 5H), 3.98 (s, 1H), 2.23 (s, 3H), 2.11 (s, 6H), 1.63 (s, 6H). $^{13}$C NMR (75 MHz, $CDCl_3$): δ 173.8, 144.5, 136.4, 134.8, 131.0, 129.0, 119.2, 116.2, 58.4, 26.2, 20.8, 18.6. IR: 3341 (m), 3310 (s), 2987 (w), 1666 (s), 1607 (m), 1488 (s), 1376 (m), 1318 (m), 1264 (m), 1210 (m), 1162 (m), 850 (m), 749 (s), 696 (m) cm$^{-1}$. HRMS Calc'd for $C_{19}H_{24}N_2O$: 297.1967. Meas: 297.1956.

A solution of the amide (100 mg, 0.337 mmol) in dry dimethoxyethane (2 ml) was added lithium aluminum hydride (80 mg, 2.1 mmol), and the mixture was refluxed for 1 day. After cooling to room temperature, the reaction was quenched by adding $H_2O$ (0.08 ml), 15% aqueous NaOH (0.08 ml), and $H_2O$ (0.24 ml) successively. The white precipitation was filtered off and the filtrate was purified by column chromatography on silica (eluent: Hexane/Ethyl acetate=10/1) to give $N^1$-mesityl-2-methyl-$N^2$-phenylpropane-1,2-diamine as a pale yellow solid (54 mg, 0.192 mmol, Y=57%). The diamine (1.45 g, 5.14 mmol) was converted to the corresponding dihydrochloride salt (1.83 g, 5.14 mmol, 100%) by treating with HCl solution (4 M in dioxane). A mixture of this salt (500 mg, 1.4 mmol) and triethyl orthoformate (4.7 ml) was stirred at 130° C. for 5 min then cooled. After cooling to room temperature, the white precipitation was collected by filtration washing with large amount of diethyl ether and then with acetone to give the desired imidazolidinium chloride salt (367 mg, 1.12 mmol, Y=80%). $^1$H NMR (300 MHz, $CDCl_3$): δ 9.76 (s, 1H), 7.65-7.62 (m, 2H), 7.49-7.47 (m, 3H), 6.92 (s, 2H), 4.13 (s, 2H), 2.39 (s, 6H), 2.27 (s, 3H), 1.69 (s, 6H). $^{13}$C NMR (75 MHz, $CDCl_3$): δ 158.4, 140.2, 134.9, 132.3, 130.2, 130.0, 129.9, 129.8, 127.4, 68.6, 63.7, 26.7, 20.9, 18.1. IR: 3401 (m), 2975 (w), 1624 (s), 1592 (m), 1301 (w), 1263 (m), 1219 (m), 856 (w), 776 (w) cm$^{-1}$. HRMS Calc'd for $C_{20}H_{25}N_2$: 293.2018. Meas: 293.2021.

Example 2

Synthesis of Ruthenium Catalysts (Phosphine Complexes, P)

General procedure: To a solution of imidazolinium salt S (1 eq) in dry benzene (or toluene) was added KHMDS (1.1 eq) under nitrogen atmosphere, and the resulting mixture was stirred at room temperature for a few minutes, after which time, $RuCl_2(PCy_3)_2(=CHC_6H_5)$ (1 eq) was added in one portion. The reaction mixture was stirred at the designated temperature and time, and then concentrated under vacuum. Dry hexane was added to the dark brown residue, and the mixture was stirred at room temperature for 20 minutes. The brown precipitation was collected by filtration and washed with hexane and then with methanol to give the desired ruthenium complexes P. Alternatively, catalysts P can be purified by column chromatography.

Example 2a $RuCl_2$(4,4-dimethyl-1,3-dimesityl-imidazolin-2-ylidene)(=CH-Ph)($PCy_3$) (P2)

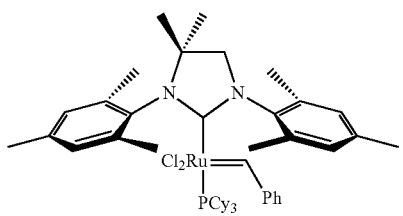

P2

Stirred at 70° C. for 1 hour. $^1$H NMR (500 MHz, $C_6D_6$, 25° C.): δ 19.72 (s, 0.45H), 19.69 (s, 0.55H), 7.32-6.96 (m, 9H), 3.33-3.12 (m, 2H), 3.09-0.95 (m, 57H). HRMS Calc'd for $C_{48}H_{69}Cl_2N_2PRu$: 876.3619. Meas: 876.3588.

Example 2b $RuCl_2$(4,4,5-trimethyl-1,3-dimesityl-imidazolin-2-ylidene)(=CH-Ph)($PCy_3$) (P4)

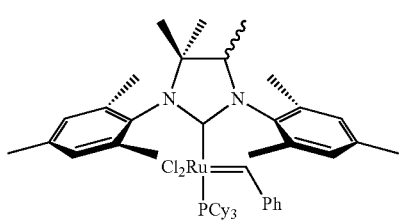

P4

Stirred at 70° C. for 1 hour. $^1$H NMR (500 MHz, $C_6D_6$, 25° C.): δ 19.69 (br s, 1H), 7.32-6.90 (m, 9H), 4.12-3.91 (m, 1H), 3.11-0.55 (m, 60H). HRMS Calc'd for $C_{49}H_{71}Cl_2N_2PRu$: 890.3776. Meas: 890.3765.

Example 2c

RuCl$_2$(4,4,5,5-Tetramethyl-1,3-diphenylimidazolin-2-ylidene)(=CH-Ph)(PCy$_3$) (P6)

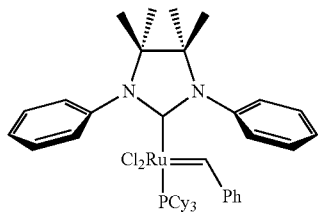

P6

Stirred overnight at RT. $^1$H NMR (500 MHz, C$_6$D$_6$): δ 19.61 (d, J=3.8 Hz, 1H), 8.11 (d, J=6.7 Hz, 2H), 7.36-6.67 (m, 13H), 2.25-2.18 (m, 3H), 1.68-1.54 (m, 15H), 1.34-1.25 (m, 6H), 1.17-1.06 (m, 9H), 0.87 (s, 6H), 0.85 (s, 6H). $^{13}$C NMR (125 MHz, C$_6$D$_6$): δ 300.8, 217.2, 216.6, 151.8, 139.3, 137.9, 133.9, 131.1, 129.5, 129.4, 129.2, 129.1, 128.9, 128.7, 128.5, 128.3, 128.0, 127.8, 127.7, 70.8, 70.7, 70.5, 33.4, 33.3, 29.6, 28.5, 28.4, 27.1, 22.5, 22.0. $^{31}$P NMR (121 MHz, C$_6$D$_6$): δ 22.35.

Example 2d

RuCl$_2$(1-Mesityl-4,4-dimethyl-3-phenylimidazolin-2-ylidene)(=CH-Ph)(PCy$_3$) (P8)

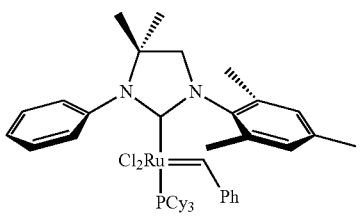

P8

Stirred overnight at RT $^1$H NMR (500 MHz, CD$_3$Cl$_2$): δ 19.14 (s, 1H), 8.77 (br s, 1H), 7.89-7.87 (m, 2H), 7.51 (t, J=7.6 Hz, 2H), 7.44 (tt, J=7.4, 1.2 Hz, 1H), 7.39 (t, J=7.4 Hz, 1H), 7.10 (t, J=7.6 Hz, 2H), 6.71 (br s, 2H), 5.84 (br s, 1H), 3.66 (br s, 2H), 2.65-1.99 (m, 5H), 1.91 (s, 3H), 1.94-1.87 (m, 3H), 1.53-1.47 (m, 9H), 1.36 (s, 6H), 1.39-1.23 (m, 6H), 0.98-0.89 (m, 16H). $^{13}$C NMR (125 MHz, CD$_2$Cl$_2$): δ 296.8, 218.1, 217.5, 151.8, 138.3, 137.7, 136.9, 136.1, 135.0, 129.7, 129.4, 129.1, 128.9, 128.6, 128.2, 65.9, 65.2, 32.7, 32.5, 29.2, 28.3, 28.2, 27.7, 26.7, 21.2, 18.8. IR (CD$_2$Cl$_2$): 2931 (s), 2852 (m), 1987 (w), 1487 (m), 1447 (m), 1400 (m), 1301 (m), 1175 (m), 778 (w) cm$^{-1}$. HRMS Calc'd for $C_{45}H_{63}Cl_2N_2PRu$: 834.3150. Meas: 834.3165.

Example 3

Synthesis of Ruthenium Catalysts (Ether Complexes, H)

General Procedures:
Procedure C:
To a solution of imidazolinium salt (1 eq) in toluene was added KHMDS (1.1 eq), and the resulting solution was stirred at room temperature for a few minutes. RuCl$_2$(PCy$_3$)(=CH-o-iPrPh) (1 eq) was then added, and the mixture was stirred for the designated time and temperature (vide infra). After cooling to room temperature, the mixture was purified by column chromatography on TSI silica (eluent: n-pentane/diethyl ether=2/1) to give the titled compounds H as a green solid Procedure D:
A mixture of phosphine complex (1 eq), o-isopropoxy-β-methylstyrene (1.5 eq), and p-toluenesulfonic acid (1.1 eq) in benzene was stirred at 40° C. for 1 hour. The mixture was cooled to room temperature, the volatiles were removed under vacuum and the residue was washed with methanol. The green solid thus obtained was recrystallized from benzene/n-pentane to give H as a dark green, crystalline solid.

Example 3a

RuCl$_2$(1,3-dimesityl-4-methyl-imidazolin-2-ylidene)(=CH-o-$^i$PrPh) (H1)

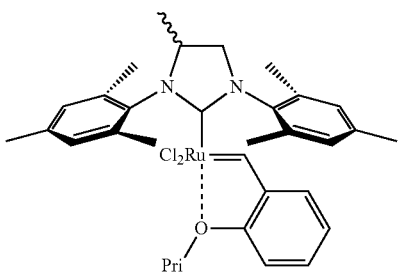

H1

Prepared according to procedure C. Stirred for 2 hours at 70° C. $^1$H NMR (500 MHz, CD$_2$Cl$_2$, 25° C.): δ 16.47 (s, 1H), 7.55 (dt, J=8.5 Hz, J=2.0 Hz, 1H), 7.10 (br s, 1H), 7.05 (br s, 3H), 6.95 (dd, J=7.5 Hz, J=2.0 Hz, 1H), 6.90 (t, J=7.5 Hz, 1H), 6.83 (d, J=8.5 Hz, 1H), 4.87 (sept, J=6.1 Hz, 1H), 4.61 (m, 1H), 4.22 (t, J=10.3 Hz, 1H), 3.77 (t, J=9.8 Hz, 1H), 2.40 (br s, 18H), 1.33 (d, J=6.5 Hz, 3H), 1.21 (m, 6H). $^{13}$C NMR (125 MHz, CD$_2$Cl$_2$): δ 296.6 (m), 212.4, 152.5, 145.8, 140.4, 139.4, 139.3, 130.4, 130.1, 129.9, 129.6, 123.0, 122.6, 113.5, 75.6, 60.2 (br), 59.7 (br), 21.8, 21.5, 21.4, 19.9 (br). HRMS Calc'd for $C_{32}H_{40}Cl_2N_2ORu$: 640.1562. Meas: 640.1578.

Example 3b

RuCl$_2$(4,4-dimethyl-1,3-dimesityl-imidazolin-2-ylidene)(=CH-o-$^i$PrPh) (H2)

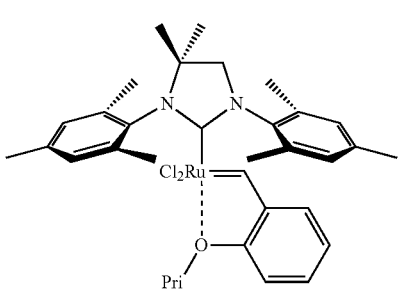

H2

Prepared according to procedure C. Stirred for 2 hours at 70° C. $^1$H NMR (500 MHz, CD$_2$Cl$_2$, 25° C.): δ 16.46 (br s, 1H), 7.55 (ddd, J=8.3 Hz, J=2.0 Hz, 1H), 7.10 (br s, 2H), 7.05

(br s, 2H), 6.95 (dd, J=7.5 Hz, J=2.0 Hz, 1H), 6.91 (t, J=7.5 Hz, 1H), 6.82 (d, J=8.0 Hz, 1H), 4.86 (sept, J=6.1 Hz, 1H), 3.93 (s, 2H), 2.50-2.25 (m, 18H), 1.47 (s, 6H), 1.21 (d, J=6.1 Hz, 6H). $^{13}$C NMR (125 MHz, C$_6$D$_6$): δ 293.0 (m), 213.3, 153.0, 146.4, 141.3, 139.0, 138.6, 130.7, 130.0, 129.3, 122.7, 122.5, 113.6, 75.4, 68.2 (br), 65.6 (br), 28.1, 21.8, 21.5, 21.4. HRMS Calc'd for C$_{33}$H$_{42}$Cl$_2$N$_2$ORu: 654.1718. Meas: 654.1725.

Example 3c

RuCl$_2$(1,3-dimesityl-4,5-dimethyl-imidazolin-2-ylidene)(=CH-o-$^i$PrPh) (H3)

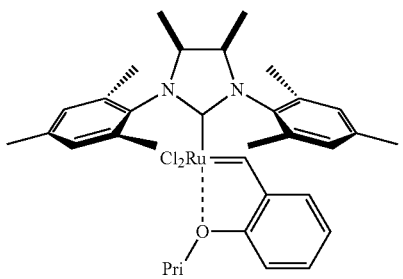

Prepared according to procedure C. Stirred for 2 hours at 70° C. $^1$H NMR (500 MHz, C$_6$D$_6$, 25° C.): δ 16.74 (s, 1H), 7.14 (dd, J=7.5 Hz, J=1.5 Hz, 1H), 7.11 (ddd, J=7.5 Hz, J=1.5 Hz, 1H), 7.00 (br s, 4H), 6.65 (dt, J=7.5 Hz, J=1.0 Hz, 1H), 6.32 (d, J=8.0 Hz, 1H), 4.49 (sept, J=6.1 Hz, 1H), 4.12 (s, 2H), 3.00-2.30 (br s, 12H), 2.25 (s, 6H), 1.31 (br s, 6H), 0.81 (d, J=6.5 Hz, 6H). $^{13}$C NMR (125 MHz, C$_6$D$_6$): δ 293.8, 213.4, 153.0, 146.4, 140.7, 138.7, 130.2, 129.9, 128.8, 122.8, 122.5, 113.6, 75.3, 62.4 (br), 21.8, 21.4, 13.9 (br). HRMS Calc'd for C$_{33}$H$_{42}$Cl$_2$N$_2$ORu: 654.1718. Meas: 654.1738.

Example 3d

RuCl$_2$(1,3-dimesityl-4,4,5-trimethyl-imidazolin-2-ylidene)(=CH-o-$^i$PrPh) (H4)

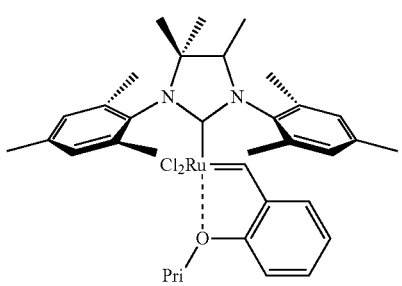

Prepared according to procedure C. Stirred for 2.5 hr at room temperature and 4 hr at 60° C. $^1$H NMR (500 MHz, C$_6$D$_6$, 25° C.): δ 16.65 (br s, 1H), 7.13-7.07 (m, 3H), 6.94 (br m, 3H), 6.63 (td, J=7.6, 0.8 Hz, 1H), 6.31 (d, J=8.0 Hz, 1H), 4.46 (sept, J=6.1 Hz, 1H), 4.20 (br s, 1H), 2.85-2.47 (m, 12H), 2.24 (s, 3H), 2.21 (s, 3H), 1.28 (d, J=6.1 Hz, 6H), 1.15 (br s, 3H), 0.88 (br s, 3H), 0.69 (br d, J=6.9 Hz, 3H). $^{13}$C NMR (125 MHz, C$_6$D$_6$): δ 293.8 (m), 213.4 (br), 152.9, 146.5, 140.7, 138.7, 138.6, 130.9, 130.6, 130.3, 129.4, 122.7, 122.4, 113.6, 75.3, 71.0 (br), 68.4 (br), 25.1, 23.1 (br), 21.8, 21.5, 21.4, 12.1. HRMS Calc'd for C$_{34}$H$_{44}$Cl$_2$N$_2$ORu: 668.1875. Meas: 668.1898.

Example 3e

RuCl$_2$[1,3-bis(2,6-difluorophenyl)-4,4,5,5-tetramethyl-imidazolin-2-ylidene](=CH-o-$^i$PrPh) (H5)

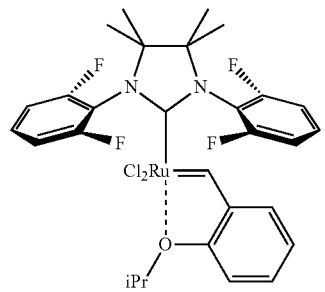

A solution of 1,3-bis(2,6-difluorophenyl)-4,4,5,5-tetramethyl-4,5-dihydro-1H-imidazol-3-ium chloride (80 mg, 0.207 mmol) in benzene (3.5 ml) was added KHMDS (45 mg, 0.224 mmol), and the resulting solution was stirred at room temperature for 10 min. To this, RuCl$_2$(PCy$_3$)(=CH-o-$^i$PrPh) (104 mg, 0.173 mmol) was added, and the mixture was stirred for 18 hr at room temperature. After evaporation, the residue was purified by column chromatography on TSI silica (eluent: n-pentane/diethyl ether=2/1~2/3) to give the titled compound as a green solid (56 mg, 0.084 mmol, Y=48%).

$^1$H NMR (300 MHz, C$_6$D$_6$): δ 16.91 (s, 1H), 7.11-7.05 (m, 3H), 6.68-6.54 (m, 6H), 6.36-6.33 (m, 1H), 4.50 (sept, J=6.2 Hz, 1H), 1.42 (d, J=6.2 Hz, 6H), 1.08 (s, 6H), 1.08 (s, 6H).

$^{19}$F NMR (282 MHz, C$_6$D$_6$): δ −106.8. HRMS Calc'd for C$_{29}$H$_{30}$Cl$_2$F$_4$N$_2$ORu: 670.0715. Meas: 670.0738.

Example 3f

RuCl$_2$[1,3-bis(phenyl)-4,4,5,5-tetramethyl-imidazolin-2-ylidene](=CH-o-$^i$PrPh) (H6)

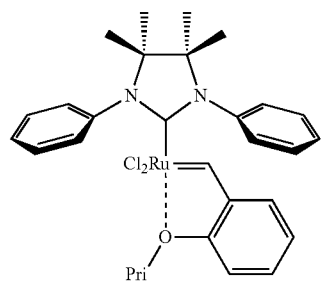

Prepared according to procedure C. Stirred for 4 hours at RT. Crystals suitable for X-ray crystallography were grown at room temperature by slow diffusion of pentane into a solution of H6 in benzene. $^1$H NMR (500 MHz, C$_6$D$_6$): δ 16.62 (s, 1H), 8.27 (d, J=7.5 Hz, 2H), 7.56 (d, J=7.1 Hz, 2H), 7.42 (t, J=7.7 Hz, 2H), 7.26 (t, J=7.3 Hz, 1H), 7.17-7.03 (m, 4H), 6.96 (dd, J=7.5, 1.6 Hz, 1H), 6.66 (t, J=7.3 Hz, 1H), 6.38 (d, J=8.3 Hz, 1H), 4.49 (sept, J=6.2 Hz, 1H), 1.38 (d, J=6.2 Hz, 6H), 0.97 (s, 6H), 0.91 (s, 6H). $^{13}$C NMR (125 MHz, C$_6$D$_6$): δ 211.0, 153.7, 144.7, 141.3, 139.5, 133.7, 131.8, 129.4, 128.9, 128.7, 128.5, 128.3, 122.6, 122.2, 113.6, 75.1, 71.3, 70.1, 22.4, 22.3.

Example 3g

RuCl$_2$[1,3-bis(o-tolyl)-4,4,5,5-tetramethyl-imidazolin-2-ylidene](=CH-o-$^i$PrPh) (H7)

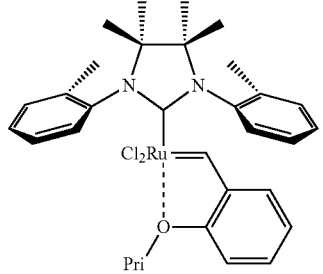

Prepared according to procedure C. Stirred for 4 hours at RT. $^1$H NMR (500 MHz, C$_6$D$_6$): δ 16.64 (s, 0.75H), 16.33 (s, 0.25H), 8.89 (d, J=7.7 Hz, 0.75H), 8.84 (d, J=7.9 Hz, 0.25H), 7.43-7.25 (m, 4H), 7.20-7.05 (m, 4H), 6.99-6.94 (m, 1H), 6.70-6.62 (m, 1H), 6.34 (d, J=8.3 Hz, 1H), 4.45 (sept, J=6.1 Hz, 1H), 2.74 (s, 0.75H), 2.68 (s, 2.25H), 2.47 (s, 0.75H), 2.44 (s, 2.25H), 1.38-1.20 (m, 10H), 1.04 (s, 2H), 0.76-0.70 (m, 6H).
$^{13}$C NMR (125 MHz, C$_6$D$_6$): δ 214.0, 211.5, 153.1, 153.0, 145.8, 143.3, 143.2, 141.6, 140.8, 140.3, 139.8, 137.3, 136.5, 136.0, 134.7, 134.4, 132.3, 132.2, 131.9, 129.6, 129.5, 129.4, 129.1, 128.9, 127.6, 127.3, 126.9, 126.6, 122.7, 122.6, 122.6, 122.5, 113.5, 75.2, 75.1, 72.3, 71.8, 71.7, 71.4, 24.9, 24.3, 24.1, 23.9, 22.7, 22.5, 22.4, 22.2, 22.1, 22.0, 20.3, 20.1, 19.7, 19.4, 19.3. HRMS Calc'd for C$_{31}$H$_{38}$Cl$_2$N$_2$ORu: 626.1405. Meas: 626.1427.

Example 3h

RuCl$_2$(1-Mesityl-4,4-dimethyl-3-phenylimidazolin-2-ylidene)(=CH-o-$^i$PrPh) (H8)

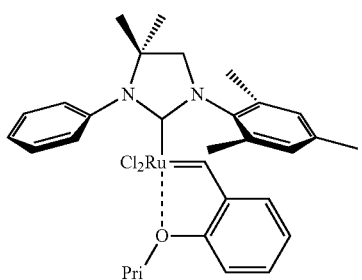

Prepared according to procedure C. Stirred for 4 hours at RT.
$^1$H NMR (500 MHz, C$_6$D$_6$): δ 16.49 (s, 0.5H), 16.48 (s, 0.5H), 7.99-7.96 (m, 2H), 7.57-7.49 (m, 4H), 7.10 (d, J=0.6 Hz, 2H), 6.91 (d, J=4.4 Hz, 2H), 6.86 (d, J=8.1 Hz, 1H), 4.90 (sept, J=6.2 Hz, 1H), 3.91 (s, 2H), 2.46 (s, 3H), 2.33 (s, 6H), 1.47 (s, 6H), 1.22 (d, J=6.2 Hz, 6H). $^{13}$C NMR (125 MHz, CD$_2$Cl$_2$): δ 297.6 (d, J$_{C-H}$=18 Hz), 209.9, 152.6, 145.1, 139.4, 138.8, 138.1, 136.5, 135.6, 130.1, 1230.0, 129.4, 128.9 (O), 128.8 (6), 122.9, 122.5, 113.4, 75.4, 66.0, 65.5, 27.8, 21.8, 21.5, 18.5. IR: 2967 (m), 1589 (m), 1572 (m), 1489 (m), 1472 (m), 1450 (m), 1380 (s), 1317 (m), 1286 (s), 1207 (m), 1179 (m), 1154 (m), 1113 (s), 1031 (w), 931 (m), 877 (w), 805 (w), 770 (w), 754 (m), 699 (m) cm$^{-1}$. HRMS Calc'd for C$_{34}$H$_{44}$Cl$_2$N$_2$ORu: 612.1249. Meas: 612. 1229.

Example 4

Standard Activity Tests of the Ruthenium Catalysts (See the Catalysts in Example 3) for Ring Closing Metathesis (RCM)

All test were performed according to the experimental procedure described by Ritter et al. (see Ritter, T.; Hejl, A.; Wenzel, A.; Funk, T. W.; Grubbs, R. H., *Organometallics*, 2006, 25, 5740.)

Preparation of a Stock Solution for the Ring Closing Metathesis (RCM) Tests:

Inside a glove box, a volumetric flask is charged with the ruthenium complex H or P (0.016 mmol) and CD$_2$Cl$_2$ or C$_6$D$_6$ was added to prepare 1.0 ml of stock solution (0.016 M).

Figure 2:
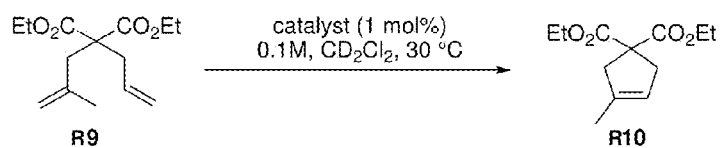
FIG. 2 depicts the standard activity tests of the Ruthenium catalysts in RCM reactions to form a tri-substituted olefin.
Figure 2:
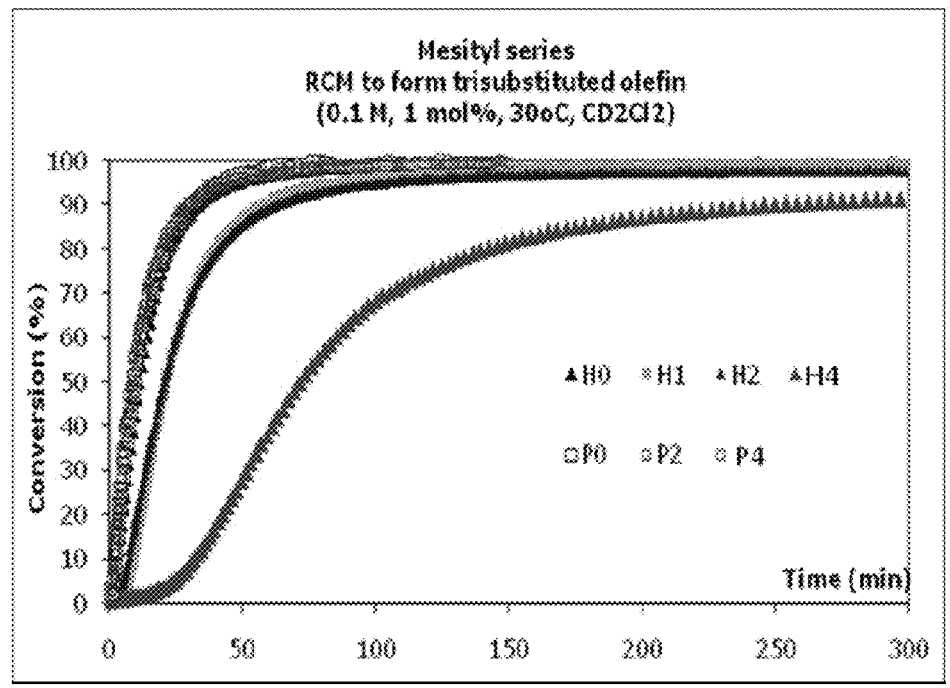

Selected Activity Test Results:

Complexes P0, P2, P4, H0, H1, H2, H4 were tested against. Catalysts P0 and H0 are described in Scholl, M.; Ding, S.; Lee, C. W.; Grubbs, R. H. *Org. Lett.* 1999, 1, 953-956; Schwab, P.; Grubbs, R. H.; Ziller, J. W. *J. Am. Chem. Soc.* 1996, 118, 100-110; and Schwab, P.; France, M. B.; Ziller, J. W.; Grubbs, R. H. *Angew. Chem., Int. Ed.* 1995, 34, 2039-2041. All complexes P and H efficiently catalyzed the RCM reactions of diethyl diallyl malonate (R7, FIG. 1) and diethyl allylmethallylmalonate (R9, FIG. 2). For complexes P, the substitution pattern does not seem to have any influence on the course of the reaction under the conditions tested. For catalysts H, the backbone substitution seems to decrease the initiation rate at 30° C.

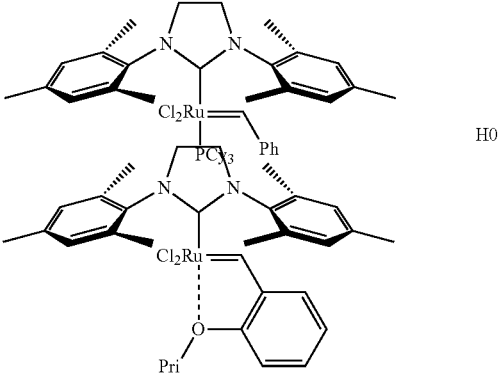

Example 4a

RCM of Diethyl Diallylmalonate (R7):

An NMR tube with a screw-cap septum top was charged inside a glovebox with catalyst stock solution (50 μL, 0.80 μmol, 1.0 mol %) and CD$_2$Cl$_2$ or C$_6$D$_6$ (750 μL). The sample was equilibrated at 30 (CD$_2$Cl$_2$) or 60° C. (C$_6$D$_6$) in the NMR probe before R7 (19.3 μL, 19.2 mg, 0.080 mmol, 0.1 M) was added via syringe. Data points were collected over an appropriate period of time using the Varian array function. The conversion to R8 was determined by comparing the ratio of the integrals of the methylene protons in the starting material, δ 2.61 (dt), with those in the product, δ 2.98 (s). At 60° C., the differences between catalysts of type H are minimal. results are shown on FIG. 1.

Example 4b

RCM of Diethyl Allylmethallylmalonate (R9):

An NMR tube with a screw-cap septum top was charged inside a glovebox with catalyst stock solution (50 μL, 0.80 μmol, 1 mol %) and $CD_2Cl_2$ or $C_6D_6$ (750 μL). The sample was equilibrated at 30 ($CD_2Cl_2$) or 60° C. ($C_6D_6$) in the NMR probe before R9 (20.5 μL, 20.4 mg, 0.080 mmol, 0.1 M) was added via syringe. Data points were collected over an appropriate period of time using the Varian array function. The conversion to R10 was determined by comparing the ratio of the integrals of the methylene protons in the starting material, δ 2.67 (s), 2.64 (dt), with those in the product, δ 2.93 (s), 2.88 (m). Results are shown on FIG. 2.

Example 5

Standard Activity Tests of the Ruthenium Catalysts H6 and H7 (See H6 and H7 in Example 3f and 3g) for Ring Closing Metathesis (RCM)

All the test were performed according to the experimental procedure described by Ritter et al. (see Ritter, T.; Hejl, A.; Wenzel, A.; Funk, T. W.; Grubbs, R. H., *Organometallics*, 2006, 25, 5740.)

Preparation of a Stock Solution for the Ring Closing Metathesis (RCM) Tests:

Inside a glove box, a volumetric flask is charged with H6 (9.6 mg, 0.016 mmol) and $CD_2Cl_2$ or $C_6D_6$ was added to prepare 1.0 ml of stock solution A (0.016 M). Stock solution B was prepared in the same manner using H7 (10.0 mg, 0.016 mmol).

Figure 3:
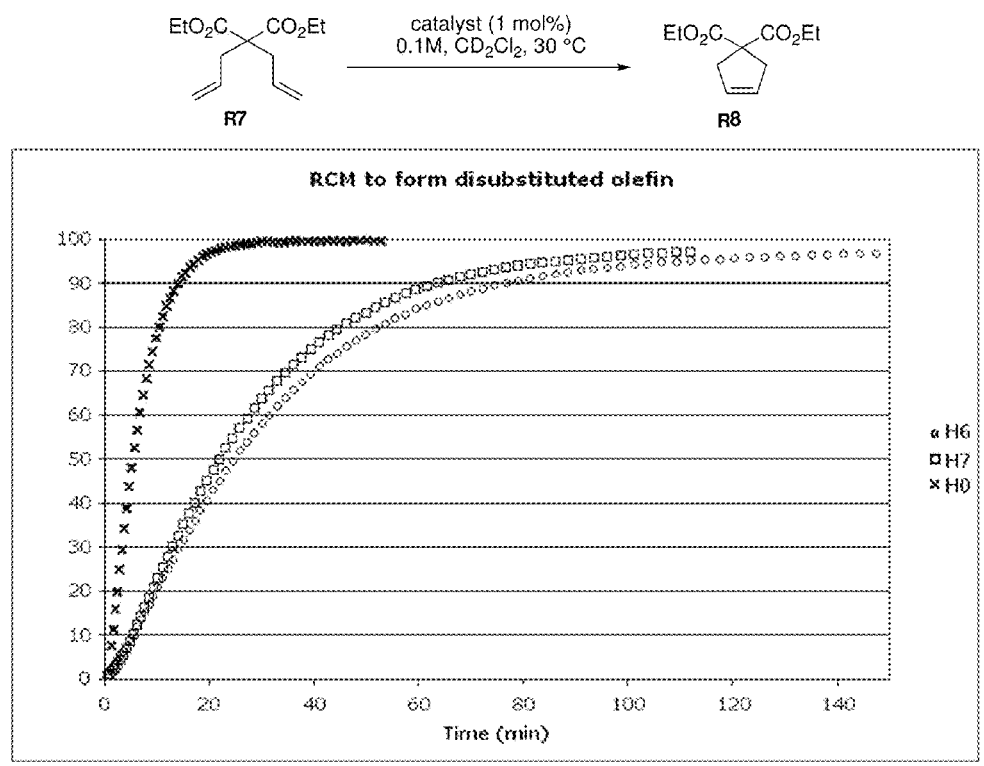
FIG. 3 depicts the standard activity tests of the Ruthenium catalysts in RCM reactions to form a di-substituted olefin.

Activity Test Results:

The complexes H6 and H7 efficiently catalyzed the RCM reactions of diethyl diallyl malonate (R7, FIG. 3) and diethyl allylmethallylmalonate (R9, FIG. 4) although there was a prolonged induction period at 30° C. compared to the known ruthenium complex H0.

Example 5a

RCM of Diethyl Diallylmalonate (R7):

An NMR tube with a screw-cap septum top was charged inside a glovebox with catalyst stock solution (50 μL, 0.80 μmol, 1.0 mol %) and $CD_2Cl_2$ or $C_6D_6$ (750 μL). The sample was equilibrated at 30 ($CD_2Cl_2$) or 60° C. ($C_6D_6$) in the NMR probe before R7 (19.3 μL, 19.2 mg, 0.080 mmol, 0.1 M) was added via syringe. Data points were collected over an appropriate period of time using the Varian array function. The conversion to R8 was determined by comparing the ratio of the integrals of the methylene protons in the starting material, δ 2.61 (dt), with those in the product, δ 2.98 (s). Results are shown on FIG. 3.

Example 5b

Figure 4:
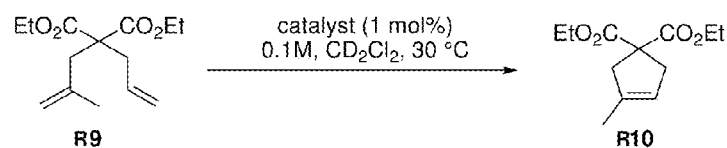
FIG. 4 depicts the standard activity tests of the Ruthenium catalysts in RCM reactions to form a tri-substituted olefin.
Figure 4:
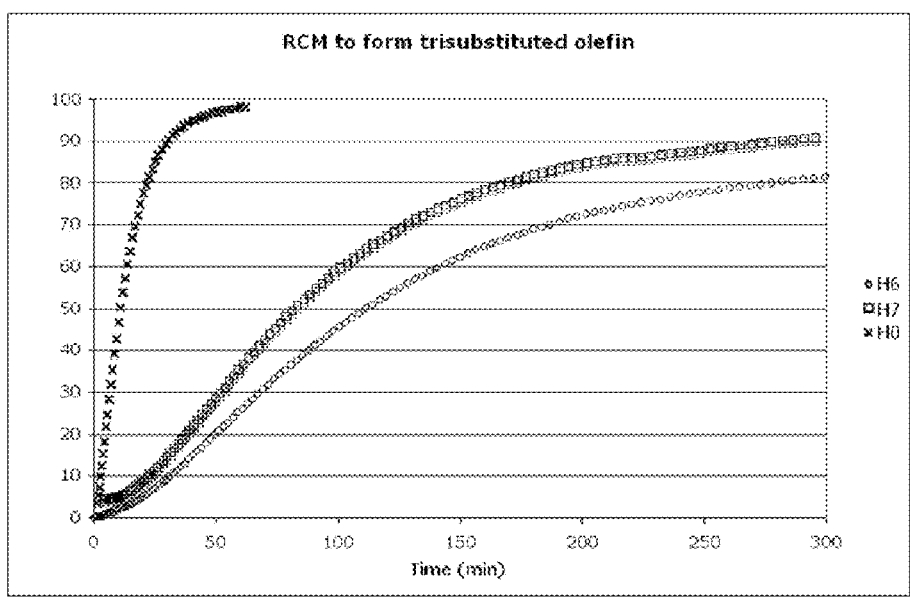

RCM of Diethyl Allylmethallylmalonate (R9, FIG. 4)

An NMR tube with a screw-cap septum top was charged inside a glovebox with catalyst stock solution (50 μL, 0.80 μmol, 1 mol %) and $CD_2Cl_2$ or $C_6D_6$ (750 μL). The sample was equilibrated at 30 ($CD_2Cl_2$) or 60° C. ($C_6D_6$) in the NMR probe before R9 (20.5 μL, 20.4 mg, 0.080 mmol, 0.1 M) was added via syringe. Data points were collected over an appropriate period of time using the Varian array function. The conversion to R10 was determined by comparing the ratio of the integrals of the methylene protons in the starting material, δ 2.67 (s), 2.64 (dt), with those in the product, δ 2.93 (s), 2.88 (m).

Figure 5:
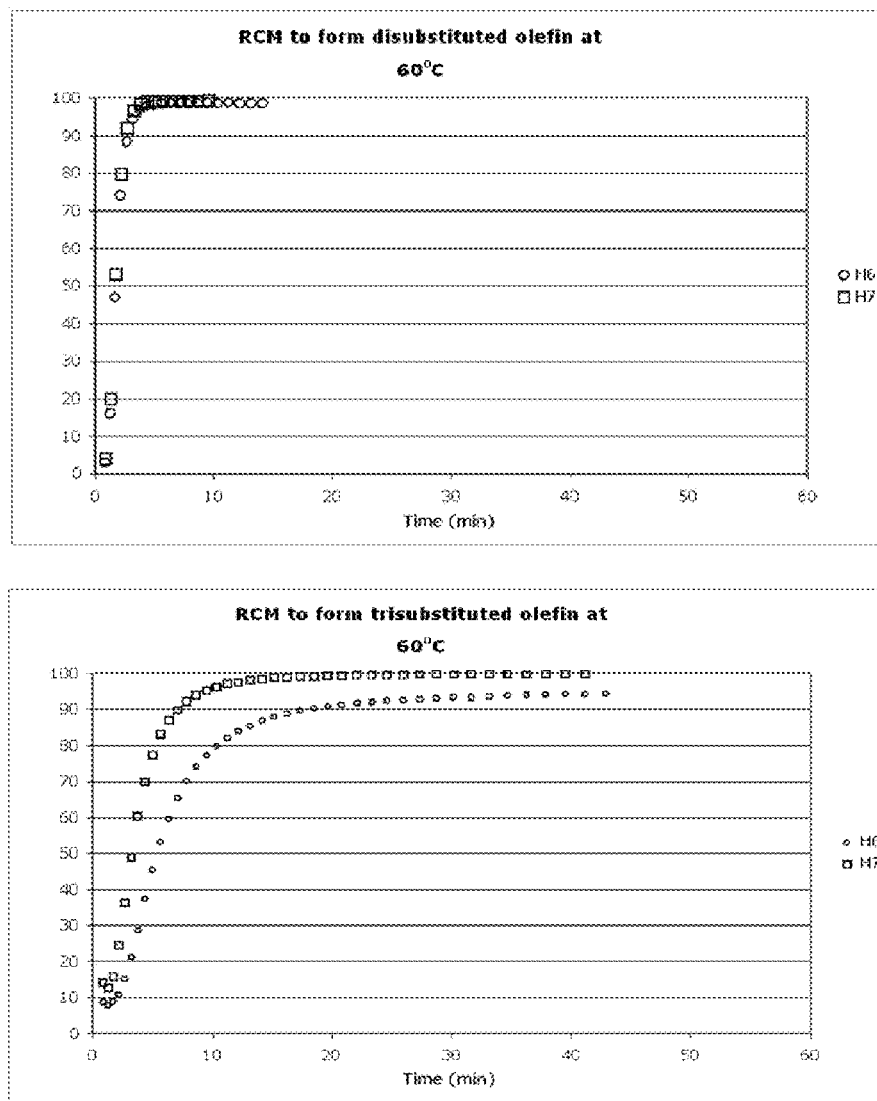
FIG. 5 depicts charts showing the standard activity tests of the Ruthenium catalysts in RCM reactions to form a di-substituted olefin and a tri-substituted olefin at 60° C.

At 60° C., both H6 and H7 initiated fast and reached 90% conversion in less than 3 minutes for RCM of R7, and less than 20 minutes for RCM of R9 (FIG. 5).

Example 5c

RCM of Diethyl Dimethallylmalonate (R11)

An NMR tube with a screw-cap septum top was charged inside a glovebox with catalyst stock solution (50 μL, 0.80 μmol, 1 mol % or 250 μL, 4.0 μmol, 5 mol %) and $CD_2Cl_2$ or $C_6D_6$ (750 or 550 μL respectively). The sample was equilibrated at 30 ($CD_2Cl_2$) or 60° C. ($C_6D_6$) in an oil bath, and R11 (21.6 μL, 21.5 mg, 0.080 mmol, 0.1 M) was added via syringe. Data points were collected over an appropriate period of time. The conversion to R12 was determined by comparing the ratio of the integrals of the methylene protons in the starting material, δ 2.71 (s) with those in the product, δ 2.89 (s).

Figure 6:
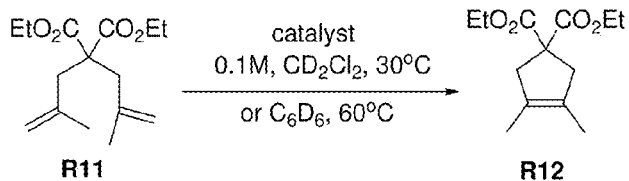
FIG. 6 depicts charts showing the standard activity tests of the Ruthenium catalysts in RCM reactions to form a tetra-substituted olefin at different temperatures.
Figure 6:
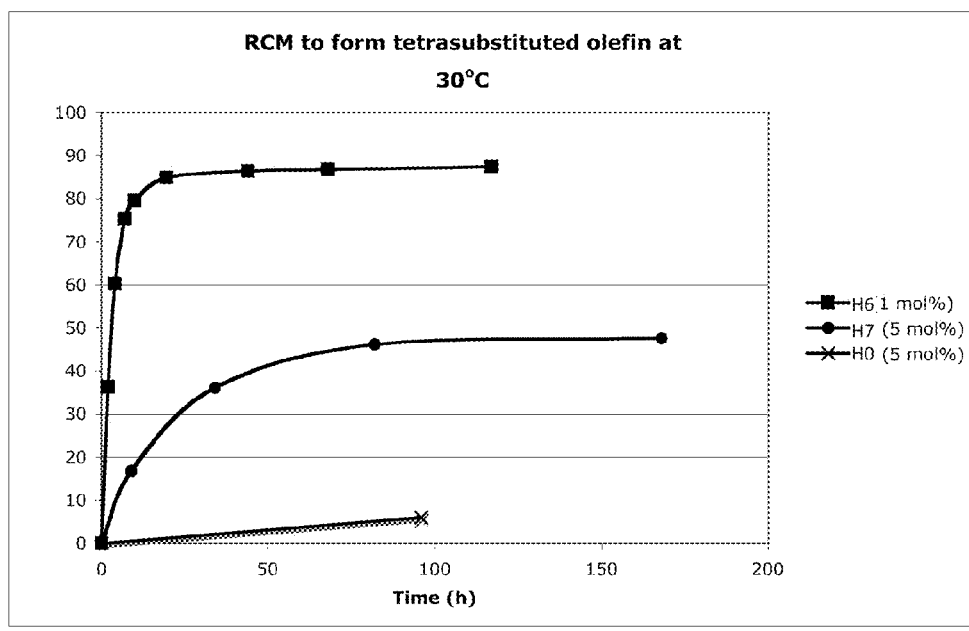
Figure 6:
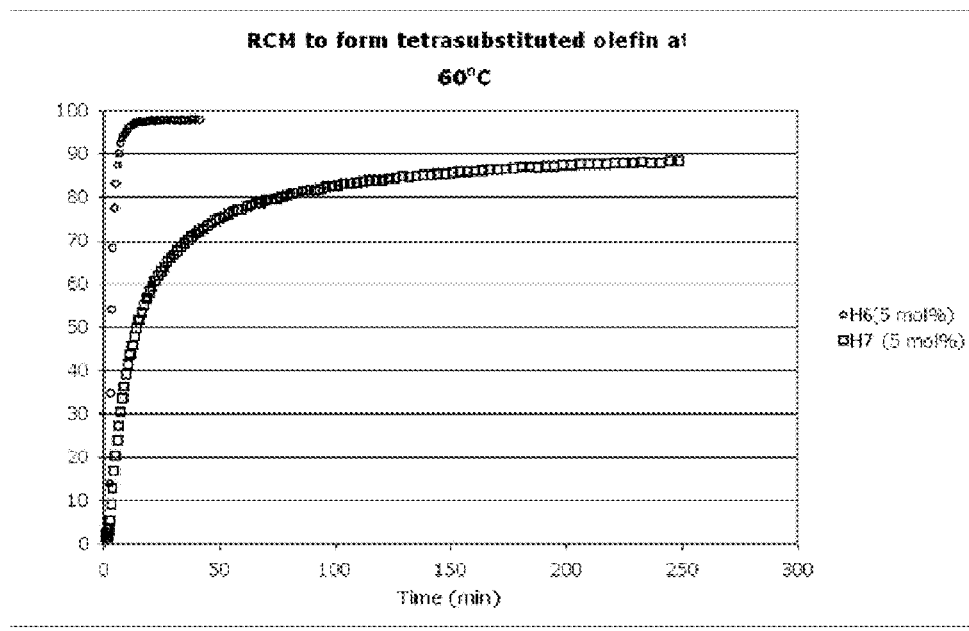

Complexes H6 and H7 proved to be very efficient catalysts for tetra-substituted olefin-forming RCM reactions, superior to the known ruthenium complex H0 as illustrated in FIG. 6. Notably, the complex H6 could catalyze this challenging reaction to give 85% conversion in 20 hours with 1 mol % of the catalyst loading. At 60° C. with 5 mol % of H6, the same reaction went completion in 20 minutes.

Example 6

Comparison of Standard Activity Tests of the Ruthenium tetra-substituted NHC complex H6 (see Example 3f) to the Ruthenium gem di-substituted NHC complex H8 (see Example 3h) for Ring Closing Metathesis (RCM), Cross Metathesis (CM) and Ring-Opening Metathesis Polymerization (ROMP) reactions.

Example 6a

RCM Reactions

Figure 7A:
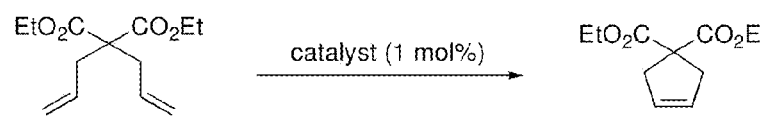
FIG. 7 depicts charts comparing the catalytic activity of compound H6 and H8 in RCM reactions to form a di-substituted olefin (FIG. 7a), a tri-substituted olefin (FIG. 7b) and a tetra-substituted olefin (FIG. 7c).
Figure 7A:
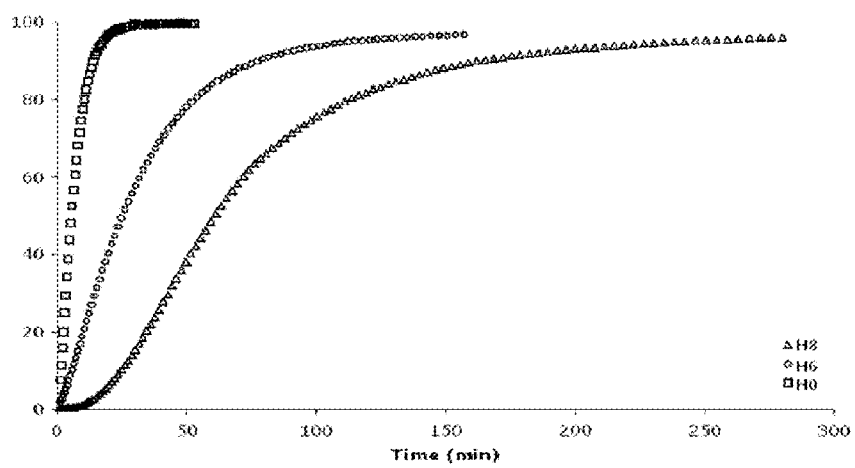
Figure 7A:
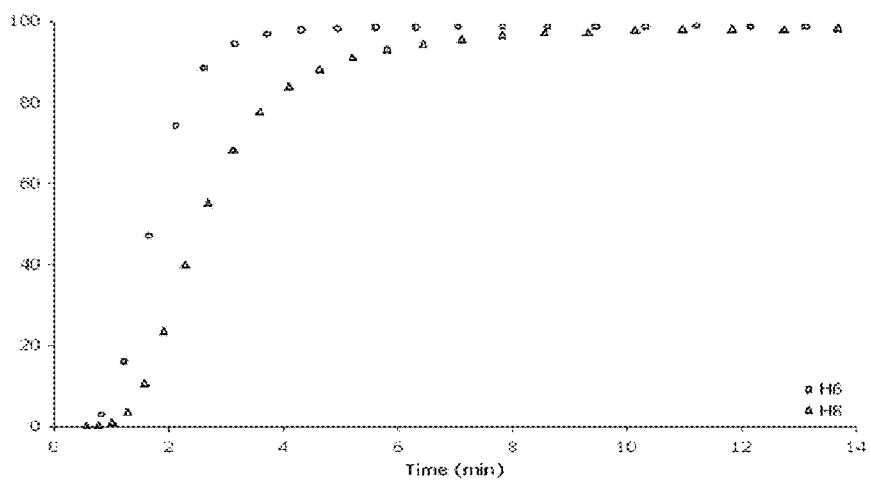
Figure 7B:
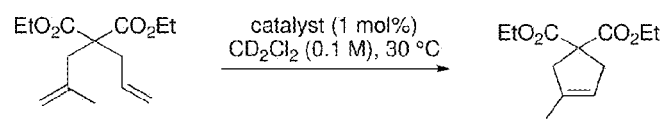
Figure 7B:
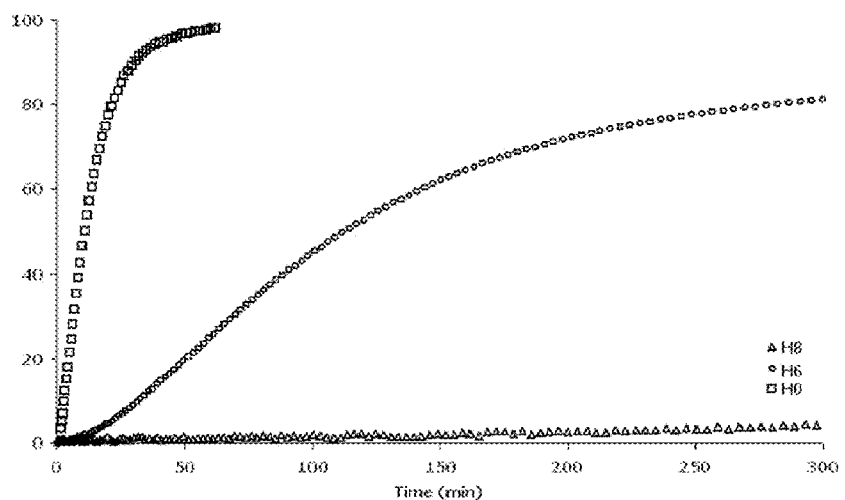
Figure 7B:
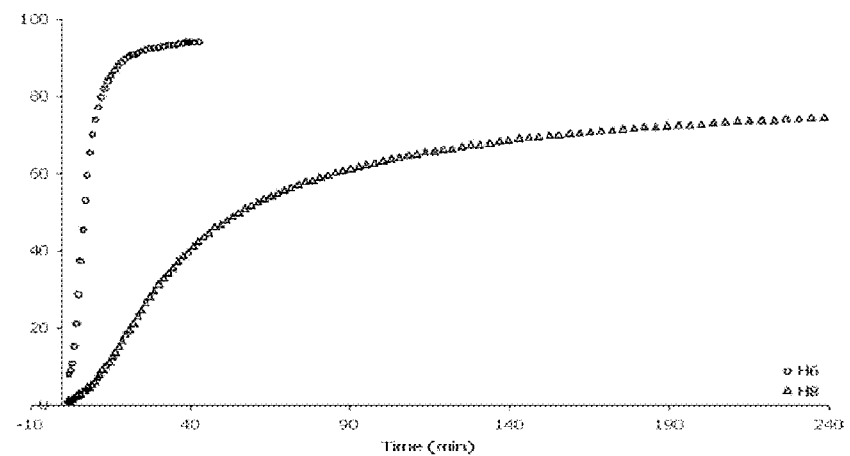
Figure 7C:
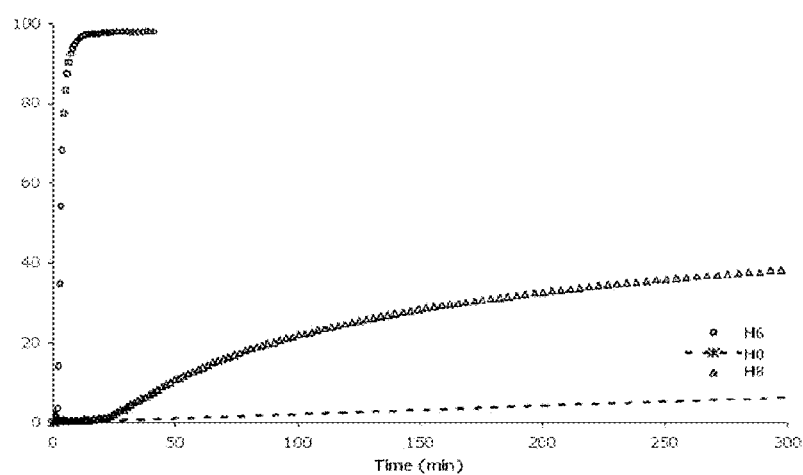

All tests were performed according to the experimental procedure described by Ritter et al. (see Ritter, T.; Hejl, A.; Wenzel, A.; Funk, T. W.; Grubbs, R. H., *Organometallics*, 2006, 25, 5740.) See FIGS. 7a, 7b and 7c.

Scheme 3. RCM Reactions with backbone substituted catalysts[a]

| Catalyst | $CD_2Cl_2$, 30° C. | $C_6D_6$, 60° C. |
|---|---|---|
| | Yield (%) | |
| 1) R7 → R8 (catalyst (1 mol %), solvent, temperature) | | |
| H0 | 99% (30 min) | |

Scheme 3. RCM Reactions with backbone substituted catalysts[a]

| Catalyst | CD$_2$Cl$_2$, 30° C. Yield (%) | C$_6$D$_6$, 60° C. |
|---|---|---|
| H6 | 95% (2 h) | 98% (5 min) |
| H8 | 95% (4 h) | 95% (10 min) |

2) R9 → R10 (catalyst (1 mol %), solvent, temperature)

| | | |
|---|---|---|
| H0 | 98% (1h) | |
| H6 | 82% (5 h) | 93% (30 min) |
| H8 | 32% (17 h) | 75% (4 h) |

3) R11 → R12 (catalyst (5 mol %), solvent, temperature)

| | | |
|---|---|---|
| H0 | 6% (96 h) | 30% (24 min) |
| H6 | 95% (4 h) | 98% (20 min) |
| H8 | no reaction | 55% (31 h) |

[a]Reactions were performed in NMR tubes with closed caps and conversions were determined by NMR.

Example 6b

Figure 8:
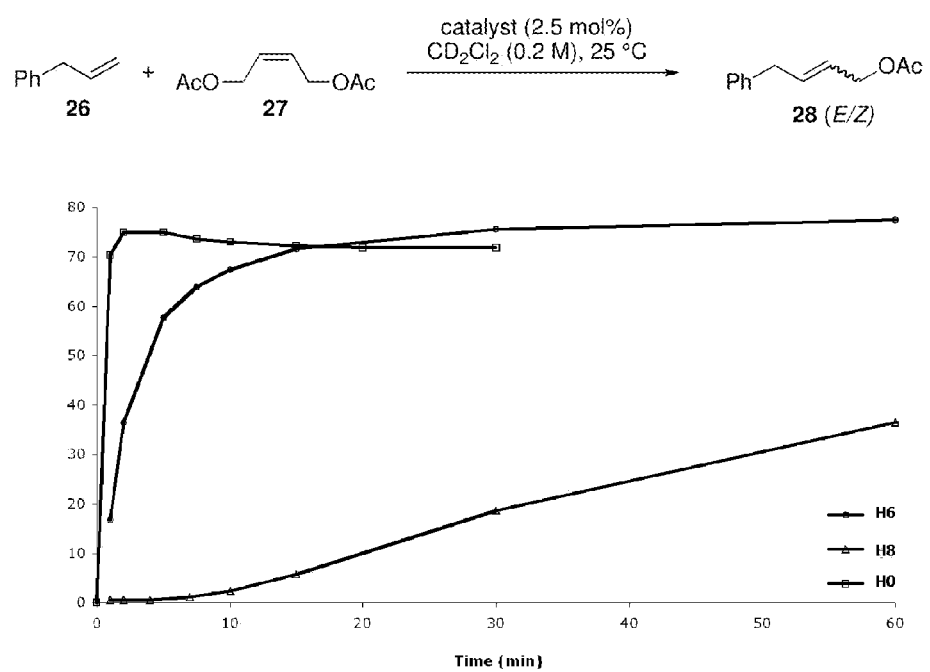
FIG. 8 depicts the catalytic activity of the Ruthenium catalysts in Cross-Metathesis (CM) reactions.

CM Reactions (see FIG. 8)

Scheme 4. Cross-metathesis[a] and ROMP[b] with backbone substitued catalysts (1) Ph⁀⁀ (26) + AcO⁀⁀⁀OAc (27) → Ph⁀⁀⁀OAc (28 (E/Z))
catalyst (2.5 mol %), CD$_2$Cl$_2$ (0.2M), 25° C.

H0 72% (10/1)
H6 78% (8/1)
H8 57% (4/1)

(2) cyclooctadiene (29) → catalyst (0.1 mol %), CD$_2$Cl$_2$ (0.5M), 30° C.

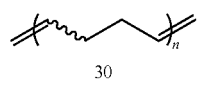

30

H0 99% (<5 min)
H6 99% (20 min)

Figure 9:
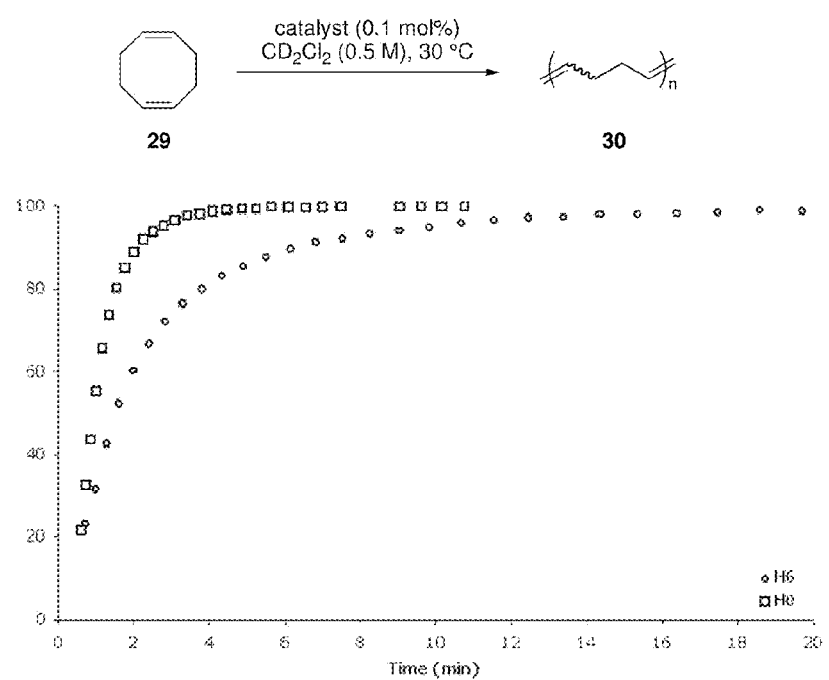
FIG. 9 depicts the catalytic activity of the Ruthenium catalysts in Ring Opening Metathesis Polymerization (ROMP) reactions.

[a] Conversion and E/Z ratio was determined by GC analysis.
[b] Reactions were performed in NMR tubes with closed caps and conversions were determined by NMR Example 6c ROMP of Cyclooctadiene (see FIG. 9)

Example 7

Figure 10:
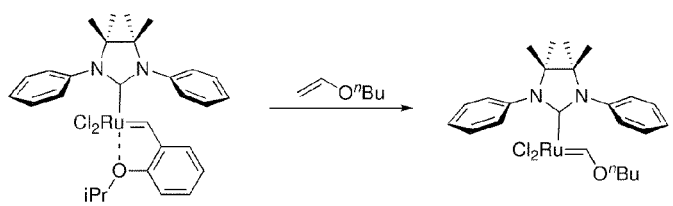
FIG. 10 depicts the initiation kinetics studies of the compound H6.
Figure 10:
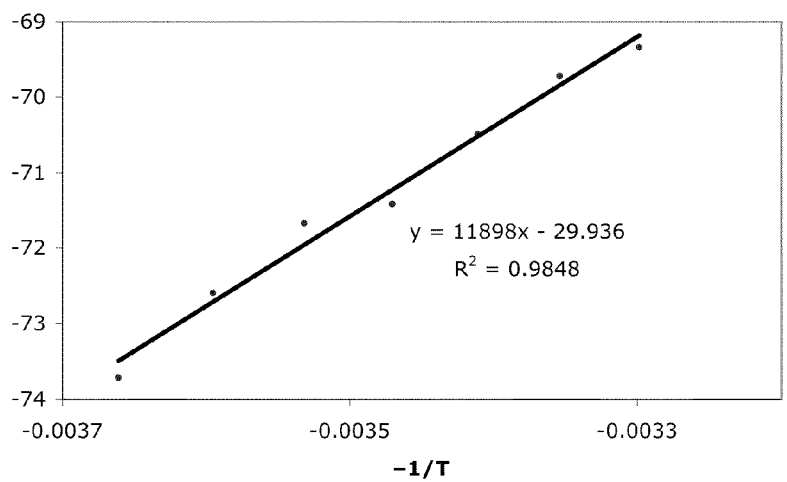

The initiation kinetics studies of compound H6 (see Example 3f). The Eyring plot is shown on FIG. 10.

The initiation kinetics studies of compound H6 were conducted according to literature procedures. (see Ritter, T.; Hejl, A.; Wenzel, A.; Funk, T. W.; Grubbs, R. H., *Organometallics*, 2006, 25, 5740.)

| (303 K) | H6 | H0 |
|---|---|---|
| ΔH$^‡$ (kcal/mol) | 11.9 (±1.7) | 15.2 (±0.8) |
| ΔS$^‡$ (e.u.) | −30 (±6) | −19 (±3) |
| ΔG$^‡$ (kcal/mol) | 21.0 (±0.1) | 20.7 (±0.01) |
| k$_{init}$ | 47 × 10$^{-4}$ | 67 × 10$^{-4}$ |

Example 8

Ring-Closing Metathesis Using Low Catalysts Loadings

Example 8a

Figure 11:
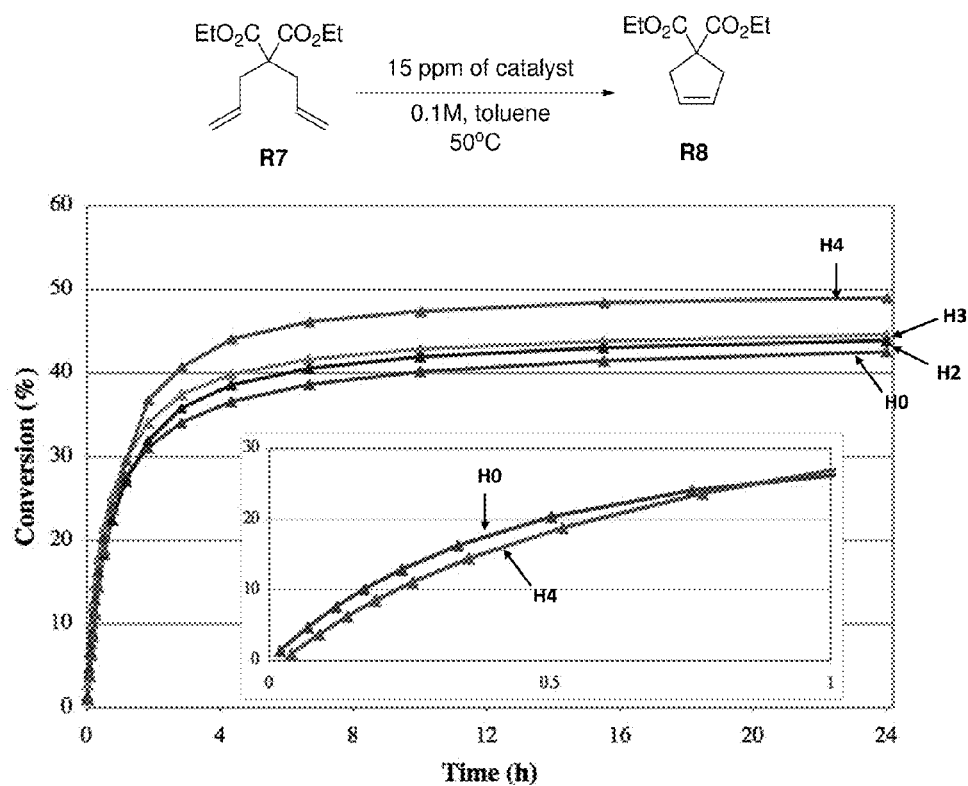
FIG. 11 depicts the catalytic activity of the Ruthenium catalysts in RCM reactions using low catalysts loadings.

H0, H2, H3, and H4 have been tested in the RCM of diethyl diallylmalonate R7 using 15 ppm of catalyst (see FIG. 11).

Example 8b

Figure 12:
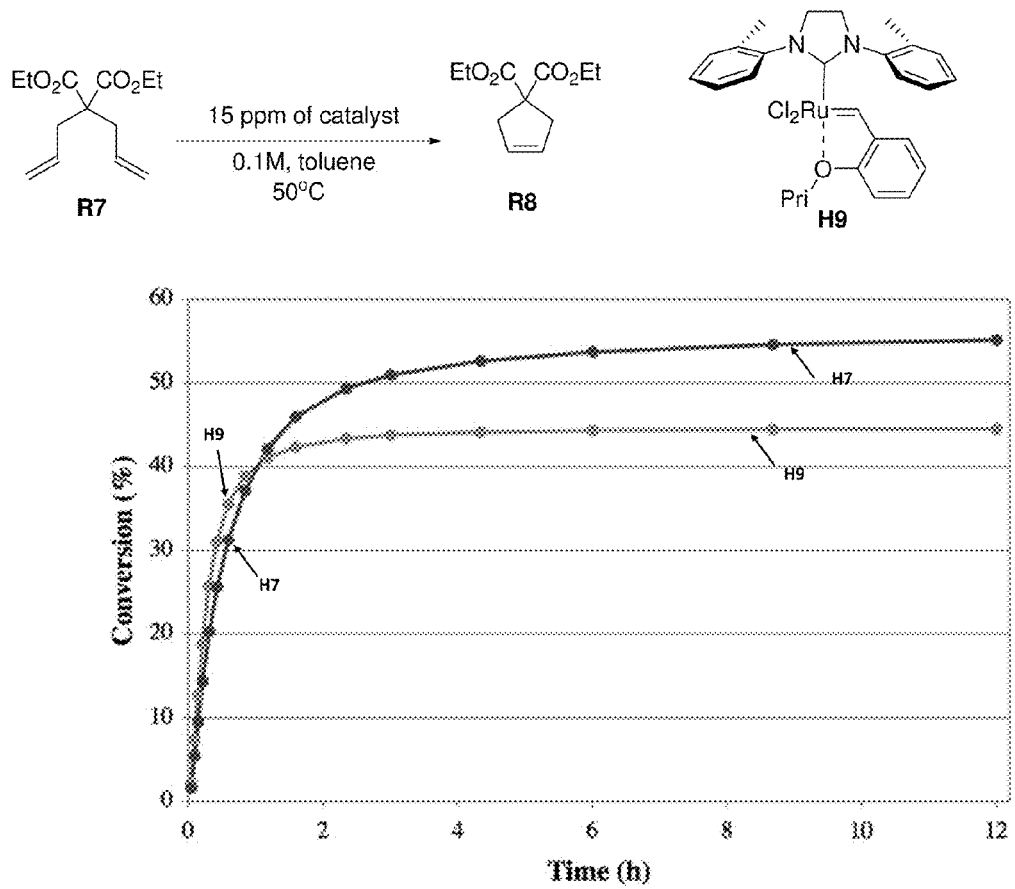
FIG. 12 depicts the catalytic activity of the Ruthenium catalysts in RCM reactions using low catalysts loadings.
Figure 13:
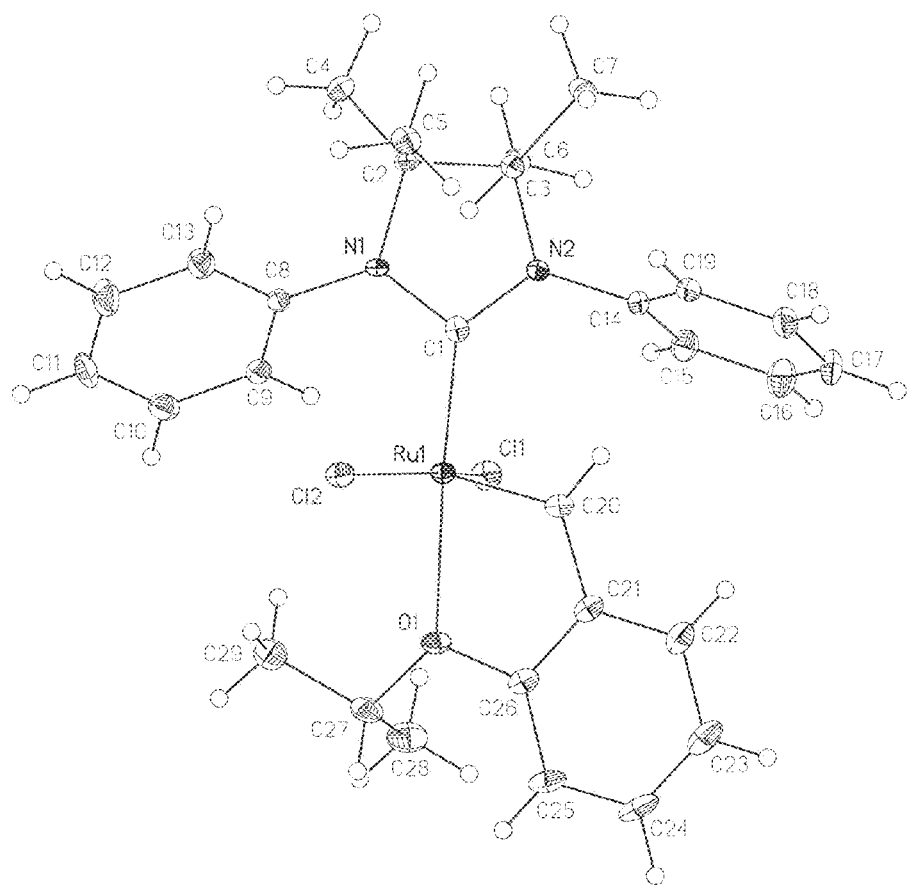
FIG. 13 depicts the X-Ray structural analysis of the compound H6.

H7 and H9 have been tested in the RCM of diethyl diallylmalonate R7 using 15 ppm of catalyst (see FIG. 12). Under those conditions, H7 leads to higher yields of R8.

Example 8c

H0, H4, H6, H7 and H9 have been tested in the RCM of R9 using 200 ppm of catalyst (Scheme 5).

Scheme 5

R9 → R10 (200 ppm of catalyst, 1M, toluene, 12 h, 50° C.)

| Catalyst | Yield (%) |
|---|---|
| H0 | 77 |
| H4 | 84 |
| H9 | 54 |
| H7 | 64 |
| H6 | 31 |

What is claimed is:

1. An imidazolinium salt of formula (I):

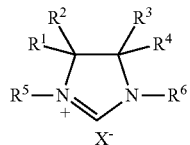

wherein:
a) $R^1$ and $R^4$ are methyl; and
   $R^2$ and $R^3$ are independently selected from methyl, ethyl, or allyl, or $R^2$ and $R^3$ together with the carbons carrying them form a fused 6-, 7- or 8-membered carbocylic ring;
   $R^5$ and $R^6$ are each independently a $C_1$-$C_{10}$ alkyl, cycloalkyl, a fused or bridged ring, aralkyl, or a group having the structure of formula (II);

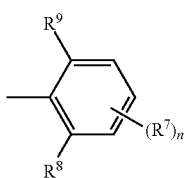

wherein,
   n ranges from 1 to 3; with the proviso that only one of $R^5$ or $R^6$ may be a linear alkyl group having 3 or less carbons;
   $R^7$ is independently selected from hydrogen, $C_1$-$C_{10}$ alkyl, $C_1$-$C_{10}$ alkoxy, aryl, aralkyl, and one or more functional groups;
   $R^8$ and $R^9$ are independently selected from hydrogen, $C_1$-$C_{10}$ alkyl, fluoride or chloride; with the proviso that $R^8$ and $R^9$ are not $C_1$-$C_{10}$ alkyl at the same time; and,
   wherein $R^2$ and/or $R^3$ may form a cyclic structure with one or both of $R^5$ and $R^6$, or through one or more links with at least one of $R^7$, $R^8$ and $R^9$;
or,
b) $R^1$ is methyl;
   $R^4$ is H;
   $R^2$ and $R^3$ are independently selected from methyl, ethyl, allyl, or isopropyl, or $R^2$ and $R^3$ together with the carbons carrying them form a fused 6-, 7- or 8-membered carbocylic ring; with the proviso that $R^2$ and $R^3$ are not both isopropyl at the same time;
   $R^5$ and $R^6$ are each independently a $C_1$-$C_{10}$ alkyl, cycloalkyl, a fused or bridged ring, aralkyl, or a group having the structure of formula (II);

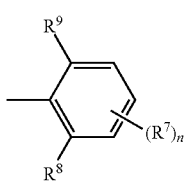

wherein,
   n ranges from 1 to 3; with the proviso that only one of $R^5$ or $R^6$ may be a linear alkyl group having 3 or less carbons;
   $R^7$ is independently selected from hydrogen, $C_1$-$C_{10}$ alkyl, $C_1$-$C_{10}$ alkoxy, aryl, aralkyl, and one or more functional groups;
   $R^8$ and $R^9$ are independently selected from hydrogen, $C_1$-$C_{10}$ alkyl, fluoride or chloride; and,
   wherein $R^2$ and/or $R^3$ may form a cyclic structure with one or both of $R^5$ and $R^6$, or through one or more links with at least one of $R^7$, $R^8$ and $R^9$;
and,
$X^-$ is an anion for the imidazolinium salt.

2. The imidazolinium salt of claim 1, wherein:
$R^1$ and $R^4$ are methyl;
$R^2$ and $R^3$ are methyl, or $R^2$ and $R^3$ together with the carbons carrying them form a fused 6-membered carbocylic ring;
$R^5$ and $R^6$ are independently selected from the group consisting of isopropyl, tertbutyl, neopentyl, phenyl, or a group a group having the structure of formula (II):

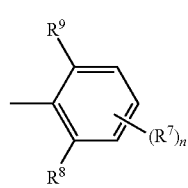

wherein n ranges from 1 to 3;
   $R^7$ is independently selected from hydrogen, $C_1$-$C_{10}$ alkyl, $C_1$-$C_{10}$ alkoxy, aryl, aralkyl, and one or more functional groups; and,
   $R^8$ and $R^9$ are independently selected from hydrogen, $C_1$-$C_{10}$ alkyl, fluoride or chloride; with the proviso that $R^8$ and $R^9$ are not $C_1$-$C_{10}$ alkyl at the same time.

3. The imidazolinium salt of claim 2, wherein:
$R^2$ and $R^3$ are methyl;
$R^5$ and $R^6$ are independently selected from phenyl, mesityl, o-tolyl, m-tolyl, p-tolyl, o-difluorophenyl, o-dichlorophenyl or o-isopropylphenyl; and,
$X^-$ is chloride, bromide, iodide, tetrafluroborate ($BF_4$) or trifluoroacetate ($CF_3COO$).

4. The imidazolinium salt of claim 1, wherein:
$R^1$ is methyl;
$R^4$ is H;
$R^2$ and $R^3$ are methyl, or $R^2$ and $R^3$ together with the carbons carrying them form a fused 6-membered carbocylic ring;
$R^5$ and $R^6$ are independently selected from isopropyl, tertbutyl, neopentyl, phenyl, or a group having the structure of formula (II):

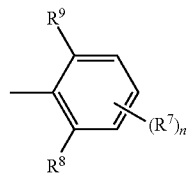

wherein n ranges from 1 to 3;
   $R^7$ is independently selected from hydrogen, $C_1$-$C_{10}$ alkyl, $C_1$-$C_{10}$ alkoxy, aryl, aralkyl, and one or more functional groups; and, $R^8$ and $R^9$ are independently selected from hydrogen, $C_1$-$C_{10}$ alkyl, fluoride or chloride.

5. The imidazolinium salt of claim 4, wherein:
$R^2$ and $R^3$ are methyl, or $R^2$ and $R^3$ together with the carbons carrying them form a fused 6-membered carbocylic ring;
$R^5$ and $R^6$ are independently selected from phenyl, mesityl, o-tolyl, m-tolyl, p-tolyl, o-difluorophenyl, o-dichloropheynl or o-isopropylphenyl; and,
$X^-$ is chloride, tetrafluroborate($BF_4$) or trifluoroacetate ($CF_3COO$).

6. The N-heterocyclic carbene (NHC) ruthenium olefin metathesis catalyst of formula (III):

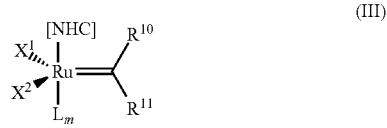

(III)

wherein:
$X^1$ and $X^2$ are independently anionic ligands;
$R^{10}$ and $R^{11}$ are each independently hydrogen or a substituted or unsubstituted substituent selected from $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl or $C_1$-$C_{20}$ alkylsulfinyl; or $R^{10}$ and $R^{11}$ may optionally be linked together to form a cyclic structure via one of the listed substituents;
m is 1 or 2, wherein, when m is 1, L is a neutral 2-electron donor ligand and may optionally be linked to $R^{11}$ forming a chelating carbene ligand; and, when m is 2, L is a heteroarene ligand; and
NHC is an N-heterocyclic carbene (NHC) ligand of formula (IV):

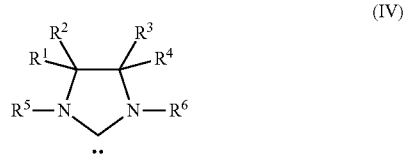

(IV)

a) $R^1$ and $R^4$ are methyl; and
$R^2$ and $R^3$ are independently selected from methyl, ethyl, and allyl, or $R^2$ and $R^3$ together with the carbons carrying them form a fused 6-, 7- or 8-membered carbocylic ring;
$R^5$ and $R^6$ are each independently a $C_1$-$C_{10}$ alkyl, cycloalkyl, a fused or bridged ring, aralkyl, or a group having the structure of formula (II):

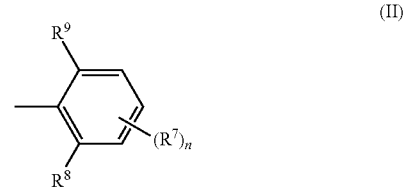

(II)

wherein,
n ranges from 1 to 3; with the proviso that only one of $R^5$ or $R^6$ may be a linear alkyl group having 3 or less carbons;
$R^7$ is independently selected from hydrogen, $C_1$-$C_{10}$ alkyl, $C_1$-$C_{10}$ alkoxy, aryl, aralkyl, and one or more functional groups;
$R^8$ and $R^9$ are independently selected from hydrogen, $C_1$-$C_{10}$ alkyl, fluoride, or chloride; with the proviso that $R^8$ and $R^9$ are not $C_1$-$C_{10}$ alkyl at the same time; and,
wherein $R^2$ and/or $R^3$ may form a cyclic structure with one or both of $R^5$ and $R^6$, or through one or more links with at least one of $R^7$, $R^8$ and $R^9$; or b) $R^1$ is methyl;
$R^4$ is H;
$R^2$ and $R^3$ are independently selected from methyl, ethyl, allyl and isopropyl, or $R^2$ and $R^3$ together with the carbons carrying them form a fused 6-, 7- or 8-membered carbocylic ring; with the proviso that $R^2$ and $R^3$ are not both isopropyl at the same time; and
$R^5$ and $R^6$ are each independently a $C_1$-$C_{10}$ alkyl, cycloalkyl, a fused or bridged ring, aralkyl, or a group having the structure of formula (II):

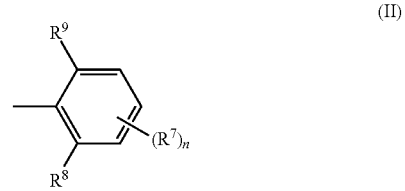

(II)

wherein,
n ranges from 1 to 3; with the proviso that only one of $R^5$ or $R^6$ may be a linear alkyl group having 3 or less carbons;
$R^7$ is independently selected from hydrogen, $C_1$-$C_{10}$ alkyl, $C_1$-$C_{10}$ alkoxy, aryl, aralkyl, and one or more functional groups;
$R^8$ and $R^9$ are hydrogen, $C_1$-$C_{10}$ alkyl, fluoride or chloride; and,
wherein $R^2$ and/or $R^3$ may form a cyclic structure with one or both of $R^5$ and $R^6$, or through one or more links with at least one of $R^7$, $R^8$ and $R^9$.

7. The N-heterocyclic carbene (NHC) ruthenium olefin metathesis catalyst of claim 6, wherein:
$R^1$ and $R^4$ are methyl;
$R^2$ and $R^3$ are methyl, or $R^2$ and $R^3$ together with the carbons carrying them form a fused 6-membered carbocylic ring; and,
$R^5$ and $R^6$ are independently selected from isopropyl, tertbutyl, neopentyl, phenyl, or a group having the structure of formula (II):

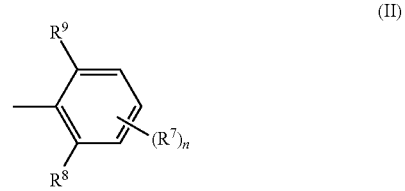

(II)

wherein,
n ranges from 1 to 3;
$R^7$ is methyl, fluoride or chloride; and,
$R^8$ and $R^9$ are as defined in claim 6.

8. The N-heterocyclic carbene (NHC) ruthenium olefin metathesis catalyst of claim 7, wherein:
  $R^2$ and $R^3$ are methyl; and
  $R^5$ and $R^6$ are independently selected from phenyl, mesityl, o-tolyl, m-tolyl, p-tolyl, o-difluorophenyl, o-dichloropheynl or o-isopropylphenyl.

9. The N-heterocyclic carbene (NHC) ruthenium olefin metathesis catalyst of claim 6, wherein:
  $R^1$ is methyl;
  $R^4$ is H;
  $R^2$ and $R^3$ are methyl, or $R^2$ and $R^3$ together with the carbons carrying them form a fused 6-membered carbocylic ring; and
  $R^5$ and $R^6$ are independently selected from isopropyl, tertbutyl, neopentyl, phenyl, or a group having the structure of formula (II):

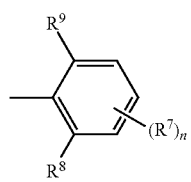

(II)

wherein,
  n ranges from 1 to 3;
  $R^7$ is methyl, fluoride or chloride; and,
  $R^8$ and $R^9$ are as defined in claim 6.

10. The N-heterocyclic carbene (NHC) ruthenium olefin metathesis catalyst of claim 9, wherein:
  $R^2$ and $R^3$ are methyl, or $R^2$ and $R^3$ together with the carbons carrying them form a fused 6-membered carbocylic ring; and,
  $R^5$ and $R^6$ are independently selected from phenyl, mesityl, o-tolyl, m-tolyl, p-tolyl, o-difluorophenyl, o-dichloropheynl or o-isopropylphenyl.

11. The N-heterocyclic carbene (NHC) ruthenium olefin metathesis catalyst of claim 6, wherein:
  $X^1$ and $X^2$ are halide, or a substituted or unsubstituted group selected from benzoate, $C_1$-$C_5$ carboxylate, $C_1$-$C_5$ alkyl, phenoxy, $C_1$-$C_5$ alkoxy, $C_1$-$C_5$ alkylthio, aryl, or $C_1$-$C_5$ alkyl sulfonate;
  $R^{10}$ is hydrogen, $C_1$-$C_5$ alkyl or aryl;
  $R^{11}$ is a substituted or unsubstituted group selected from $C_1$-$C_{20}$ alkyl, $C_2$-$C_{20}$ alkenyl, or aryl;
  m is 1; and,
  L is selected from phosphine, sulfonated phosphine, phosphite, phosphinite, phosphonite, arsine, stibine, ether, amine, amide, imine, sulfoxide, carboxyl, nitrosyl, pyridine, or thioether, or is linked to $R^{11}$ forming a chelating carbene ligand.

12. The N-heterocyclic carbene (NHC) ruthenium olefin metathesis catalyst of claim 11, wherein:
  $X^1$ and $X^2$ are each halide, $CF_3CO_2$, $CH_3$, $CO_2$, $CFH_2CO_2$, $(CH_3)_3$ CO, $(CF_3)_2$ $(CH_3)CO$, $(CF_3)(CH_3)_2CO$, PhO, MeO, EtO, tosylate, mesylate, or trifluoromethanesulfonate;
  $R^{10}$ is hydrogen, $C_1$-$C_5$ alkyl or aryl;
  $R^{11}$ is a substituted or unsubstituted group selected from the group consisting of $C_1$-$C_{20}$ alkyl, $C_2$-$C_{20}$ alkenyl, and aryl;
  m is 1; and,
  L is a phosphine of the formula PR'R"R''', where R', R", and R''' are each independently aryl, $C_1$-$C_{10}$ alkyl, or $C_3$-$C_6$ cycloalkyl, or is linked to $R^{11}$ forming a chelating carbene ligand.

13. The N-heterocyclic carbene (NHC) ruthenium olefin metathesis catalyst of claim 12, wherein:
  $X^1$ and $X^2$ are each chloride;
  $R^{10}$ is hydrogen;
  $R^{11}$ is phenyl, vinyl or —CH=C(CH$_3$)$_2$;
  m is 1; and
  L is selected from P(cyclohexyl)$_3$, P(cyclopentyl)$_3$, P(isopropyl)$_3$, or P(phenyl)$_3$, or is linked to $R^{11}$ forming a chelating carbene ligand.

14. The N-heterocyclic carbene (NHC) ruthenium olefin metathesis catalyst of claim 6, wherein the catalyst of formula (III) has the structure of formula (V):

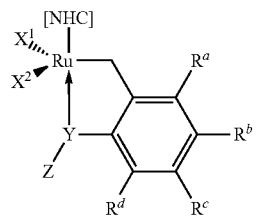

(V)

wherein,
  NHC is an N-heterocyclic carbene (NHC) ligand of formula (IV), as defined in claim 6;
  Y is a heteroatom selected from oxygen, sulfur, nitrogen, or phosphorus;
  $X^1$ and $X^2$ are independently anionic ligands;
  Z is selected from hydrogen, alkyl, alkenyl, alkynyl, aryl, alkoxy, alkenyloxy, alkynyloxy, aryloxy, functionalized alkyl, or functionalized aryl, wherein the functional group(s) may independently be selected from alkoxy, aryloxy, halogen, carbonyl, carboxylic acid, ketone, aldehyde, nitrate, nitrile, nitro, cyano, isocyanate, hydroxyl, ester, ether, amine, imine, amide, sulfide, sulfonyl, sulfinyl, disulfide, sulfonate, carbamate, silane, siloxane, phosphine, phosphate, borate, or combinations thereof; each optionally substituted with an alkyl, halogen, alkoxy, aryl, aryloxy, or heteroaryl moiety;
  $R^a$, $R^b$, $R^c$, and $R^d$ are independently selected from hydrogen, halogen, alkyl, alkenyl, alkynyl, aryl, heteroaryl, alkoxy, alkenyloxy, alkynyloxy, aryloxy, functionalized alkyl, or functionalized aryl, wherein the functional group(s) may independently be selected from alkoxy, aryloxy, halogen, carbonyl, carboxylic acid, ketone, aldehyde, nitrate, nitrile, nitro, cyano, isocyanate, hydroxyl, ester, ether, amine, imine, amide, sulfide, sulfonyl, sulfinyl, disulfide, sulfonate, carbamate, silane, siloxane, phosphine, phosphate, borate, or combinations thereof; each optionally substituted with an alkyl, halogen, alkoxy, aryl, aryloxy, or heteroaryl moiety, wherein any two or more of $R^a$, $R^b$, $R^c$, and $R^d$ may be independently linked through hydrocarbon or functionalized hydrocarbon groups forming an aliphatic or aromatic ring.

15. The N-heterocyclic carbene (NHC) ruthenium olefin metathesis catalyst of claim 13, wherein the catalyst of formula (III) is selected from:

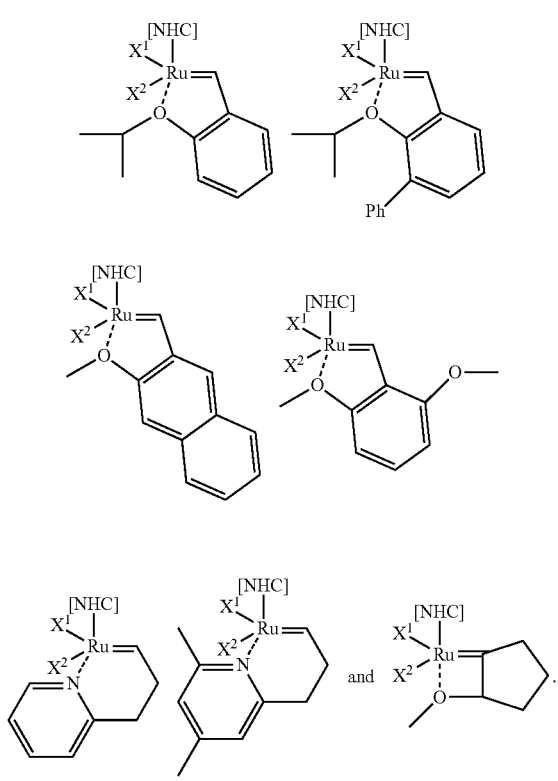

16. The N-heterocyclic carbene (NHC) ruthenium olefin metathesis catalyst of claim 11, wherein the catalyst of formula (III) is selected from:

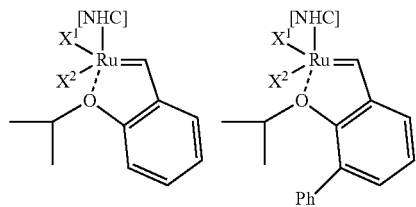

-continued

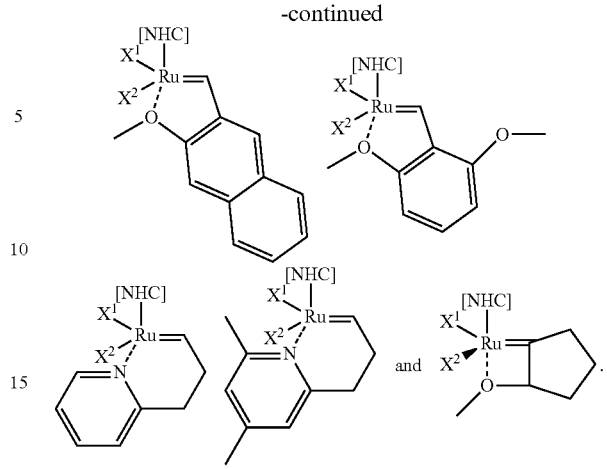

17. The N-heterocyclic carbene (NHC) ruthenium olefin metathesis catalyst of claim 13, wherein L is selected from P(cyclohexyl)$_3$, P(cyclopentyl)$_3$, P(isopropyl)$_3$, or P(phenyl)$_3$.

18. The N-heterocyclic carbene (NHC) ruthenium olefin metathesis catalyst of claim 11, wherein L is selected from P(cyclohexyl)$_3$, P(cyclopentyl)$_3$, P(isopropyl)$_3$, or P(phenyl)$_3$.

19. A ring-closing metathesis method for preparing a tetrasubstituted cyclic olefin comprising:
    contacting an olefinic compound having at least two terminal olefins which are substituted at the beta-carbon of each terminal olefin with an N-heterocyclic carbene (NHC) ruthenium olefin metathesis catalyst of claim 6 under metathesis conditions to form a cyclic tetra-substituted olefin.

20. The method of claim 19 wherein the catalyst is present in an amount ranging from about 25 ppm to about 10 mol %.

21. An olefin metathesis reaction comprising the step of:
    contacting an olefin with an N-heterocyclic carbene (NHC) ruthenium olefin metathesis catalyst of claim 6 under metathesis conditions.

22. A cross-metathesis reaction comprising the step of contacting an olefin and a tri-substituted olefin or a di-substituted olefin having further substitution at the allylic carbon with an N-heterocyclic carbene (NHC) ruthenium olefin metathesis catalyst of claim 6 under metathesis conditions.

* * * * *

UNITED STATES PATENT AND TRADEMARK OFFICE
CERTIFICATE OF CORRECTION

PATENT NO.         : 8,877,936 B2
APPLICATION NO.    : 12/936917
DATED              : November 4, 2014
INVENTOR(S)        : Robert H. Grubbs et al.

Page 1 of 1

It is certified that error appears in the above-identified patent and that said Letters Patent is hereby corrected as shown below:

In the Specification

Column 1, Line 8 replace:
"GOVERNMENT SUPPORT
This invention was supported by National Institutes of Health under Grant number GM031332. The U.S. government has certain rights in this invention."

With:
--GOVERNMENT SUPPORT
This invention was made with government support under Grant No. GM031332 awarded by the National Institutes of Health. The government has certain rights in the invention.--

Signed and Sealed this
Fifth Day of September, 2017

Joseph Matal
*Performing the Functions and Duties of the*
*Under Secretary of Commerce for Intellectual Property and*
*Director of the United States Patent and Trademark Office*